United States Patent
Chen et al.

(10) Patent No.: US 11,938,283 B2
(45) Date of Patent: Mar. 26, 2024

(54) BENDABLE SHEATH AND DELIVERY SYSTEM USING BENDABLE SHEATH

(71) Applicant: VENUS MEDTECH (HANGZHOU), INC., Zhejiang (CN)

(72) Inventors: Mao Chen, Hangzhou (CN); Yuan Feng, Hangzhou (CN); Zhifei Zhang, Hangzhou (CN); Feng Guo, Hangzhou (CN); Quangang Gong, Hangzhou (CN); Shiguang Wu, Hangzhou (CN)

(73) Assignee: VENUS MEDTECH (HANGZHOU), INC., Hangzhou (CN)

( * ) Notice: Subject to any disclaimer, the term of this patent is extended or adjusted under 35 U.S.C. 154(b) by 852 days.

(21) Appl. No.: 17/010,415

(22) Filed: Sep. 2, 2020

(65) Prior Publication Data

US 2021/0008344 A1    Jan. 14, 2021

Related U.S. Application Data

(63) Continuation of application No. PCT/CN2019/070146, filed on Jan. 2, 2019.

(30) Foreign Application Priority Data

Jan. 3, 2018 (CN) .......................... 201810003498.5
Mar. 22, 2018 (CN) .......................... 201810242064.0

(51) Int. Cl.
  *A61M 25/01* (2006.01)
  *A61F 2/24* (2006.01)
  *A61M 25/00* (2006.01)

(52) U.S. Cl.
  CPC ......... *A61M 25/0147* (2013.01); *A61F 2/243* (2013.01); *A61M 25/0023* (2013.01);
  (Continued)

(58) Field of Classification Search
  CPC . A61F 2/2436; A61F 2/2427; A61M 25/0147; A61M 25/0136; A61M 2025/0024; A61M 2025/0681
  See application file for complete search history.

(56) References Cited

U.S. PATENT DOCUMENTS

2008/0065011 A1* 3/2008 Marchand ............. A61F 2/2436
                                                    604/103.05
2015/0202410 A1  7/2015 Odeh
2016/0158497 A1* 6/2016 Tran .................. A61M 25/0147
                                                    604/95.04

FOREIGN PATENT DOCUMENTS

CN     103446655 A    12/2013
CN     104096309 A    10/2014
(Continued)

*Primary Examiner* — Bradley J Osinski
(74) *Attorney, Agent, or Firm* — Raymond Sun

(57) ABSTRACT

A bendable sheath and a delivery system using the bendable sheath. The bendable sheath comprises a tube body (3). The tube body (3) comprises a distal end and a proximal end. A tube wall of the tube body (3) is connected to a pull wire (8). One end of the pull wire (8) extends towards the proximal end of the tube body (3), and the other end is connected to the tube body (3) near the distal end of the tube body (3). The pull wire (8) comprises at least a section thereof disposed freely outside the tube body (3) and near the distal end of the tube body (3). The pull wire (8) in the bendable sheath comprises the section disposed freely outside the sheath tube body (3) and, when pulled, the section is disposed so as to facilitate the application of force. The section moves relative to the tube body (3), such that a force application point is adaptively changed. The present invention improves the safety and flexibility of operations when there is a large bending radius, or when using long, hard, or inflexible intervention apparatuses.

17 Claims, 30 Drawing Sheets

(52) U.S. Cl.
CPC . *A61M 25/0136* (2013.01); *A61M 2025/0024* (2013.01); *A61M 2205/04* (2013.01); *A61M 2210/125* (2013.01)

(56) References Cited

FOREIGN PATENT DOCUMENTS

| | | |
|---|---|---|
| CN | 205964665 A | 2/2017 |
| CN | 206081103 U | 4/2017 |
| CN | 206792433 U | 12/2017 |
| WO | WO2015/010963 A1 | 1/2015 |

\* cited by examiner

BENDABLE SHEATH AND DELIVERY SYSTEM USING BENDABLE SHEATH

TECHNICAL FIELD

The disclosure relates to the technical field of medical instruments, and in particular, to a bendable sheath and a delivery system using the bendable sheath.

BACKGROUND

Interventional surgery causes little trauma to the human body and is less invasive, and is a medical technique that has rapidly emerged and promoted in recent years. It usually requires an implantable medical sheath such as a delivery sheath, a guiding sheath, or the like, to provide a channel between the lesion site of the patient and the operator for delivering medical treatment instrument, medicine, an implantable instrument or the like to the lesion site. The implantable medical sheath has a distal end and a proximal end. The distal end can enter the vasculature of the human body. The proximal end is connected with the operating handle. During operation, a guiding channel is generally provided in advance, and the distal end of the sheath or another auxiliary instrument connected thereto punctures into the blood vessel. The operator controls the distal end of the sheath through the operating handle to advance along the pre-determined guiding channel to the lesion site to release medicine, instrument, or the like.

Considering the complicated human vasculatures and the long-distance operation, the sheath should generally have sufficient axial and radial supporting force and good compliance. Before reaching the lesion site, the distal end of the pushed sheath which has a good compliance advances along the guiding channel and is able to adaptively adjust the bending direction to conform to the veins of the human body. Due to the influence of blood flow in the blood vessel, the sheath usually advances along the blood vessel wall, which, in the early stage, almost has no influence on the advance of the sheath. However, when medicine and instruments are released, the distal end of the sheath is required to be directed to the lesion site. Obviously, in this case, the direction of the distal end of the sheath must be adjusted and controlled to move the distal end of the sheath to the target position.

Heart valve replacement is taken as an example here. The heart valve of the human body is located in the center of the blood vessel. When the heart valve needs to be replaced, the distal end of the sheath needs to reach the center of the valve, and then the heart valve replacement device carried on the sheath is released to replace the native valve. Because the sheath advances along the blood vessel wall, it is necessary to adjust the direction of the distal end of the sheath to move towards the center of the valve to approach the lesion site. For example, the diameter of the aortic valve is about 26 mm, and the diameter of the blood vessel there is obviously larger than the diameter of the aortic valve. In general, the diameter of the distal end of the sheath is about 7 mm, so that the distal end of the sheath must be moved at least about 9 mm in the diameter direction of the blood vessel.

One solution is to shape the distal end of the sheath according to the distribution of human blood vessels or the structures of the human body. The sheaths are customized in shape according to different distributions and structures to meet the requirement for reaching the lesion site in the circuitous blood vessel. For example, US patent publication No. 2003/144657 discloses a sheath assembly that includes an outer sheath with a pre-shaped distal end and an inner sheath with a pre-shaped end. The inner and outer sheaths, which can be rotated with respect to each other, provide a sheath assembly the shape of the distal end of which is adjustable, to improve the implantation of the coronary sinus which is implanted using the sheath and positioned by the right atrium. However, this sheath does not adapt to the personalized physiological anatomy of a patient, and would affect the efficacy of surgery.

At present, a common solution is to use a sheath with an adjustable distal end, which usually includes one or more pull wires (also called traction wires). The distal end of the pull wire is fixed to the distal end of the sheath, and the pull wire extends along the side wall of the sheath to the proximal end of the sheath, and is connected to the adjustment mechanism on the handle at the proximal end of the sheath. The pull wire can slide in the sheath to allow the operator to positively change the curvature of the sheath. Specifically, the distal end of the sheath is bent, and is guided to advance to the target site.

For example, the Chinese patent No. CN102921089A discloses a controllable bendable sheath for the interventional therapy of the head. The head of the sheath with multiple chambers is connected with a flexible head of the main sheath, and the tail of the sheath with multiple chambers is connected with an extension tube through a connector. A handle is provided outside the extension tube, and a slidable device is movably connected in the handle. The slidable device abuts against the extension tube. The upper and lower ends of the slidable device extend outside the housing of the handle. The upper and lower sides of the slidable device are respectively connected with a pull wire. The other end of the pull wire passes through the chamber of the sheath with multiple chambers that is located at the same side with the flexible head of the main sheath, and is fixedly connected to the flexible head of the main sheath. The other end of the extension tube extends outside of the handle and is connected with a joint. After the sheath enters the human body, depending on the structure of the blood vessels or related parts, the pull wire is controlled by the handle. The pull wire, which is pulled by the pulling force from the slidable device, pulls the flexible head of the main sheath at the distal end of the sheath. The flexible head of the main sheath is bent backwards by the pulling force from the pull wire, so as to adjust the direction of the flexible head of the main sheath.

Even if the pull wire is known in the prior art, the entire pull wire runs within and is constrained within a passage or a channel where it is located. Therefore, in the case where the sheath is required to be bent to a great extent, or in the case where the implantable instrument surrounded by the distal end of the sheath is long and rigid, it is difficult to achieve a desired bending effect. Furthermore, due to the limitations of the applied force and the deformation of the pull wire under the influence of the neighboring parts during bending, the operation is more laborious.

SUMMARY

The present disclosure provides a bendable sheath, which facilitates the adjustment of the distal end of the sheath, and improves the controllability of the bending direction of the distal end of the sheath. The distal end of the sheath can be easily controlled to bend or move towards a predetermined lesion site.

A bendable sheath may include a tube and a pull wire. The tube has a distal end and a proximal end, and the distal end of the tube is configured to be bent by the pull wire. One end of the pull wire extends towards the proximal end of the tube, a connection portion of the other end of the pull wire and the tube is located at or adjacent to the distal end of the tube, and at least one section of the pull wire is configured as a movable section which is movable outside of the tube.

The distal end of the pull wire may be fixed and adjacent to the distal end of the tube, and the proximal end of the pull wire extends out of the tube for connection with an operating handle. The pull wire itself may be made of a metal wire or polymer fiber or the like that is thin and meets the strength requirements. The material and the processing method of the pull wire can use existing techniques.

Several alternative implementations are also provided below, but they are not intended as additional limitations to the above-mentioned technical solution. The following is merely provided as additional or preferable embodiments. Without technical or logical contradiction, the alternative implementations can be combined with the above-mentioned technical solution, separately or in combination.

Preferably, the bendable sheath is further provided with a guiding member which functions between the tube and the movable section to delimit a gap between the tube and the movable section during bending.

Preferably, a plurality of the guiding members is provided which are spaced-apart from each other in an axial direction of the tube to form a plurality of guiding portions for delimiting the gap between the tube and the movable section.

The guiding member is configured as a radial expandable structure, and has an undeformed configuration in which the guiding member constrains the movable section against an outer wall of the tube, and a deformed configuration in which the guiding member is locally separated from the tube under the influence of the movable section.

Preferably, the guiding member is continuously distributed in an axial direction of the tube to form a guiding channel for delimiting the gap between the tube and the movable section.

Preferably, the guiding member is configured as a guiding sleeve that is connected around an outer periphery of the tube and surrounds the movable section.

The guiding sleeve is made of a flexible material, and has an undeformed configuration in which the guiding sleeve drives the movable section against an outer wall of the tube, and a deformed configuration in which the guiding sleeve is locally separated from the tube under the influence of the movable section.

The guiding sleeve is configured as a coiled structure, and has a deformed configuration in which the guiding sleeve is locally separated from the tube under the influence of the movable section and the corresponding portions of the coiled structure are unfolded, and an undeformed configuration in which the coiled structure automatically returns to drive the movable section to closely contact with an outer wall of the tube.

The coiled structure in the undeformed configuration is coiled by more than one circle, and a portion extending beyond 360 degrees overlaps with a portion within 360 degrees.

A starting end and a terminal end of the coiled structure that is coiled in a circumferential direction are connected by a flexible film.

The guiding sleeve in the undeformed configuration surrounds and constrains the movable section against the outside of the tube.

Preferably, at least a part of the guiding sleeve is fixed to the tube. Preferably, a distal end and a proximal end of the guiding sleeve are fixed on the outer periphery of the tube, and a section of the guiding sleeve between the distal end and the proximal end is movably arranged around the outer periphery of the tube.

Preferably, at least a part of the movable section is located within a radial gap between the tube and the guiding sleeve. More preferably, the entire movable section is located within the radial gap between the tube and the guiding sleeve.

Preferably, the movable section is movably arranged within the radial gap between the tube and the guiding sleeve.

Preferably, the movable section is locally and slidably engaged on an inner side of the guiding sleeve. Further, the guiding sleeve has a double-layered structure and a part of the movable section extends in the double-layered structure, or the movable section is movably stitched on the guiding sleeve.

Preferably, the guiding sleeve surrounds a part of the tube in a circumferential direction; or the guiding sleeve is cylindrical and surrounds the tube one circle in a circumferential direction.

Preferably, the tube comprises an expandable section at the distal end for accommodating an implantable instrument, and a connection section connected to the expandable section and extending towards the proximal end, wherein a distal end of the guiding sleeve is:

fixed on the connection section adjacent to the expandable section; or fixed at a junction of the connection section and the expandable section; or fixed on the expandable section and adjacent to a proximal end of the expandable section.

Preferably, a side wall of the guiding sleeve is provided with a reinforced area that contacts and engages with the movable section.

Preferably, the reinforced area has a larger thickness relative to the other neighboring area.

Preferably, a reinforcement layer is provided in a side wall of the reinforced area.

Preferably, the tube comprises an expandable section at the distal end for accommodating an implantable instrument, and a connection section connected to the expandable section and extending towards the proximal end, wherein a distal end of the movable section is:

fixed on the connection section adjacent to the expandable section; or fixed at a junction of the connection section and the expandable section; or fixed on the expandable section.

Preferably, the distal end of the movable section is fixed on the expandable section, and is close to a proximal end of the expandable section, or is close to a distal end of the expandable section, or is between the proximal end and the distal end of the expandable section.

Preferably, a distal end of the movable section is fixedly connected to at least one of an outer wall, an inner wall, and an intermediate layer of the tube.

Preferably, the tube comprises an expandable section at the distal end for accommodating an implantable instrument, and an expandable section connected to the expandable section and extending towards the proximal end; wherein a metal reinforcing structure is provided in an intermediate layer of the expandable section, and a distal end of the movable section enters the intermediate layer of the expandable section and is fixedly connected with the metal reinforcing structure.

Preferably, a distal end of the movable section is fixed to the tube by knotting, welding or bonding.

Preferably, a distal end of the movable section is configured to enter an inner cavity of the tube from an outer wall of the tube through a first through hole, and then pass out of the tube from the inner cavity through a second through hole, and is thereafter knotted with a portion of the movable section outside the tube.

Preferably, the first through hole is closer to the distal end of the tube, or closer to the proximal end of the tube, or at the same axial position on the tube relative to the second through hole.

Preferably, one single movable section or multiple movable sections spaced-apart from each other are provided.

Preferably, a section of the pull wire between two adjacent movable sections is configured as a transition section, and the transition section extends inside the tube.

Preferably, the tube is at least provided with a reinforcing frame at the transition section.

Preferably, a sleeve is provided outside the tube, and the sleeve is axially and slidably engaged with the tube, and the sleeve is closer to the proximal end of the tube relative to the guiding member.

Preferably, the tube comprises an expandable section at the distal end for accommodating an implantable instrument, and a connection section connected to the expandable section and extending towards the proximal end, wherein the sleeve is located around an outer periphery of the connection section.

Preferably, a section of the pull wire connected to a proximal end of the movable section is configured as an extension section, and the extension section extends towards the proximal end within the gap between the tube and the sleeve.

Preferably, a section of the pull wire connected to a proximal end of the movable section is configured as an extension section, and a connection portion of the movable section and the extension section passes through a wall of the tube, and the extension section extends towards the proximal end inside the tube.

Preferably, a proximal end of the guiding sleeve and a distal end of the sleeve are adjacent to or connected to each other.

Preferably, the proximal end of the guiding sleeve and the distal end of the sleeve are connected to each other and are formed in one single piece.

Preferably, the movable section of the pull wire is located at or adjacent to the distal end of the tube.

The pull wire is movable outside of the tube and is connected to the distal end of the tube. The pull wire directly controls the tube and transmits a pulling force more effectively.

Preferably, the pull wire is connected at the distal end of the tube, or less than 5 cm away from the distal end, further preferably, less than 3 cm. A longer distance would affect the pulling and bending performance.

Preferably, the movable section of the pull wire extends from the middle of the tube to the distal end of the tube, or to a position adjacent to the distal end of the tube.

The longer the movable section, the less the constraint force from the sheath. The requirements for the controlling force can be reduced, and at the same time, the requirements for the limit pressure of the stressed structural parts, connectors, and connecting points can be reduced.

Preferably, the movable section of the pull wire extends from the proximal end of the tube to the distal end of the tube, or to a position adjacent to the distal end of the tube.

The completely independent pull wire would not be affected by the bent tube and directly control the distal end. The tube bends in the delivery path.

Different sheaths have different structures at their distal ends. In the case where the structure at the distal end is not suitable for loading the pull wire, the connection point of the pull wire may be shifted to an appropriate position, and then the distal end can be moved by the pull wire.

The movable section is relative to the existing pull wire which extends entirely in a channel or cavity in the prior art. The movable section is usually floatable outside the tube, or at least has a great degree of freedom, and can be separated from the outer wall of the tube to a certain extent in order to maintain the tensioning effect.

The movable section can also limit the entire pull wire to a certain extent, such as limiting the distance of the entire pull wire separating from the outer wall of the tube, or limiting the inclined angle of the entire pull wire relative to the axial direction of the tube.

The sheath of the present disclosure can be used for the delivery of blood vessel stents, heart valve stents or other implantable instruments.

In order to improve safety, an anti-cut protective layer is provided around the outside of the movable section.

The anti-cut protective layer may be made of relatively flexible material to avoid cutting the body tissues when the pull wire is tensioned. The anti-cut protective layer and the pull wire may be fixed relative to each other, or may also be slidable relative to each other, provided that the anti-cut protective layer would not produce an adverse effect on pulling the tube.

Preferably, more than two pull wires are provided. More preferably, connection portions of the more than two pull wires and the tube are evenly distributed around a circumferential direction of the tube.

In order to improve the connection between the pull wire and the tube, preferably, the end of the pulling wire is provided with a loop, and the loop surrounds an outer periphery of the tube.

The tube may be pulled by the loop to avoid local stress concentration.

The loop is fixed on an outer wall of the tube, or rotatably surrounds the outer wall of the tube and is limited in an axial direction.

The loop can be fixed on the outer wall of the tube by welding, or via a connector. The loop rotatably surrounds the outer wall of the tube, which facilitates the adaptive adjustment of the stressed portion of the pull wire during bending.

For the axial limiting, the outer wall of the tube is provided with an axial limiting groove, and the loop is rotatably received in the axial limiting groove.

For the axial limiting, the outer wall of the tube is provided with an axial limiting member, and both axial sides of the loop are blocked by the axial limiting member.

Preferably, the axial limiting member is configured as a blocking hook or a guiding ring. One or more axial limiting members may be provided to limit the axial position of the loop.

Preferably, the axial limiting member is configured as a limiting step on the outer wall of the tube, or as a limiting ring fixed on the tube.

In order to cooperate with the profile of the sheath during pulling and to determine the appropriate stressed portions, more than two pull wires, such as 2, 3, or 4 pull wires, may be provided. In the case where only one pull wire is provided, which is fixed relative to the tube, if the pull wire or the loop can change the circumferential position relative to the tube, the pull wire can adaptively adjust its stressed portion by pulling.

Preferably, the loop is fixed on an outer wall of the tube, and the loop is connected with 2 to 4 pull wires that are evenly distributed in a circumferential direction.

In the case where the loop is fixedly connected to the tube, the loop may be fixed on the outer wall of the tube or built in the side wall of the tube.

Preferably, the loop and the pull wire are formed in one piece, or are configured as two separate pieces which are fixedly connected or detachably connected.

In the case where the loop and the pull wire are formed in one piece, the pull wire itself may be coiled with its distal end to form a closed ring, and fixed with itself. In other words, the pull wire itself is coiled with a distal end thereof to form the loop.

In the case where the loop and the pull wire are configured as two separate pieces, in order to improve the strength, the loop may be slightly wide in the axial direction. For example, the width of the loop in the axial direction may be in a range of 1 mm to 5 mm. After being unfolded, the loop generally presents as a flat strip.

In order to further control the profile of the sheath delivered in the human body to cooperate with the bending process, preferably, a reinforcing rib is further fixed in a side wall the tube.

Preferably, the tube is provided with a channel in the side wall, the reinforcing rib extends in the channel to the distal end, and a wall of the channel and the reinforcing rib are fixed to each other.

Preferably, two reinforcing ribs are provided, and the pull wire and the reinforcing ribs are spaced-apart from each other in a circumferential direction of the tube.

More preferably, two pull wires and two reinforcing ribs are provided, and the two reinforcing ribs are arranged opposite to each other relative to an axis of the tube; a center angle between any of the reinforcing ribs and one of the pull wires on any cross section of the tube is in the range of 30 degrees to 150 degrees.

Preferably, the center angle between any of the reinforcing ribs and one of the pull wires on any cross section of the tube is in the range of 80 degrees to 100 degrees.

Preferably, the pull wires and reinforcing ribs may be evenly distributed in the circumferential direction of the tube.

Here, because one section of the pull wire is movable, the position of the pull wire may be regarded as the connection portion of the pull wire and the tube. Since the connection portion of the pull wire and the tube may be changeable, it is specified that the connection portion refers to the fixed connection portion of the pull wire and the tube.

If the connection portion of the pull wire and the tube is changeable, for example, the pull wire is connected to the tube by the loop which is rotatably installed, the pull wire will adaptively adjust its stressed portion to reach the optimal pulling position and bend the tube.

The two reinforcing ribs may be respectively on the opposite sides of the axis of the tube, that is, the two reinforcing ribs may be respectively on opposite sides of the tube, so that the sheath will not be easily bent in the direction of the line connecting the two reinforcing ribs in the radial direction, and can only be bent in the direction of the center line perpendicular to the line connecting the two reinforcing ribs. When the pulling wire is pulled, the distal end of the sheath will be inevitably and more easily bent in the most flexible manner (towards the direction of the pulling wire).

Alternatively, the two reinforcing ribs may not be arranged opposite to each other. The central angle corresponding to the two reinforcing ribs on any cross section of the tube may be less than 180 degrees, and the pull wire is located on the side of the line connecting any reinforcing rib and the axis of the tube along the radial direction. In this way, the sheath will not be bent in the radial direction between each reinforcing rib and the axis of the tube. Therefore, the pull wire should be arranged to avoid being distributed on the radial line between any reinforcing rib and the axis of the tube.

The distal end of the tube may be an expandable section for accommodating an implantable instrument. The connection portion of the pull wire may be adjacent to the distal end of the expandable section.

In order to facilitate the extending of the pull wire and the constraint to the pull wire, in addition to the movable section, the non-movable section of the pull wire may extend toward the proximal end through a guiding element. The guiding element may be additionally provided or be formed by the tube itself.

The distal end of the tube is an expandable section for accommodating an implantable instrument, and the pull wire is connected to the proximal end of the expandable section.

The implantable instrument may be, for example, valves.

A section of the pull wire adjacent to the distal end is configured as an imaging section.

The imaging section may be made of materials containing developing components, or may be provided in the form of a built-in material, external coating, covering, or the like so as to be observed by a medical imaging system.

The length of the imaging section may be greater than the length of the movable section.

The length of the imaging section is in a range of 12 cm to 20 cm.

The imaging section has a sufficient length to indicate the turning position when the sheath is bent, so as to determine the approximate turning angle and direction.

The imaging section is configured to form a developing area that is continuously distributed, or to form a plurality of developing points that are spaced-apart from each other.

The present disclosure also provides a bendable delivery system for an implantable valve including the bendable sheath, a sheath core arranged in the bendable sheath, and an operating handle connected to proximal ends of the bendable sheath and the sheath core; wherein a proximal end of the pull wire is connected with the operating handle.

The sheath core comprises a core tube, and the core tube has a loading section at a distal end for placing the implantable instrument; before release, an expandable section of the bendable sheath is configured to surround the loading section.

The core tube is fixed with a guiding head at the distal end, and a fixing head for the implantable instrument adjacent to the guiding head, wherein the loading section is between the guiding head and the fixing head for the implantable instrument.

Preferably, the operating handle includes:
a fixed body with a hollow structure;
a pulling member slidably installed in the fixed body and connected with the pull wire;
a driving mechanism installed on the fixed body for driving the pulling member to move;
a control mechanism installed on the fixed body for driving the bendable sheath to move.

Preferably, the driving mechanism includes:
a movable member that abuts against the pulling member in an
axial direction to exert a force;
an adjustable knob that surrounds the fixed body and is rotatable around an axis of the fixed body, wherein, the adjustable knob is cylindrical and surrounds an outer periphery of the movable member, and the adjustable knob and the movable member are in a threaded engagement.

Preferably, a distal end side of the fixed body is fixed with a front handle, and the front handle is provided with a hollow axial guiding groove, and a part of the movable member extends out of the axial guiding groove which is provided with external threads, and the adjustable knob is provided with internal threads engaged with the external threads.

Preferably, at least two axial guiding grooves are provided, which are evenly distributed around an axis of the fixed body.

Preferably, the driving mechanism is configured as a linear actuator and is connected with the pulling member for transmitting movement.

Preferably, the control mechanism includes:
a control handle which is rotatably installed outside the fixed body, and has internal threads in an inner wall;
a transmission rod which is slidably mounted in the fixed body along the axis of the fixed body, and is provided with linkage teeth engaged with the internal threads of the control handle, and the tube of the bendable sheath is connected with the transmission rod.

Preferably, the fixed body is provided with a guiding groove for guiding the linkage teeth to move in an axial direction.

Preferably, the pulling member is configured as an annular structure, and the transmission rod slidably passes through a central area of the pulling member.

Preferably, the movable member is configured as an annular structure and abuts against a distal end of the pulling member, and the transmission rod slidably passes through the center area of the pulling member.

Preferably, the control handle is provided with a limiting member that limits an axial displacement of the transmission rod.

Preferably, the limiting member is movably mounted on the control handle, and has a limiting configuration in which the limiting member abuts against the linkage teeth and a release configuration in which the limiting member avoids the linkage teeth.

Preferably, a side wall of the control handle is provided with an installation opening, and the limiting member is movably received in the installation opening.

Preferably, the limiting member is configured as an adjustable wheel which is rotatably installed;
an axial end surface of the adjustable wheel is configured as a limiting surface, and the limiting surface blocks a movement path of the linkage teeth in the limiting configuration;
the adjustable wheel is provided with an avoidance groove on an outer periphery, and the avoidance groove corresponds to the movement path of the linkage teeth in the release configuration.

Preferably, at least a part of the outer periphery of the adjustable wheel is located outside the installation opening, and an anti-slip structure is provided on the part of the outer periphery of the adjustable wheel.

Preferably, the adjustable wheel is provided with a mark indicating configurations of the limiting member.

The pull wire in the bendable sheath of the present disclosure has a section that is movable outside of the tube of the sheath, and has a profile that facilitates the application of force when being pulled. In the case where a sheath is required to be bent to a great extent, or in the case where the implantable instrument is long, rigid and not easy to be bent, since the pull wire is movable relative to the tube, and also its stressed portion can be adaptively changed, the safety and flexibility of the operation are improved.

DETAILED DESCRIPTION OF THE EMBODIMENTS

The technical solutions in the embodiments of the present disclosure will be clearly and completely described below in conjunction with the accompanying drawings in the embodiments of the present disclosure. Obviously, the described embodiments are only a part of the embodiments of the present disclosure, not all of the embodiments. Based on the embodiments of the present disclosure, all other embodiments obtained by those skilled in the art without inventive work shall fall within the protection scope of the present disclosure.

It should be noted that when a component is "connected" with another component, it may be directly connected to the other component or may be indirectly connected to another component through a further component. When a component is "provided" on another component, it may be directly provided on another component or may be provided on another component through a further component.

Unless otherwise defined, all technical and scientific terms used herein have the same meaning as commonly understood by those skilled in the art. The terms used in the specification of the present disclosure herein is only for the purpose of describing specific embodiments, not for limiting the present disclosure. The term "and/or" as used herein includes any and all combinations of one or more related listed items.

Figure 1:
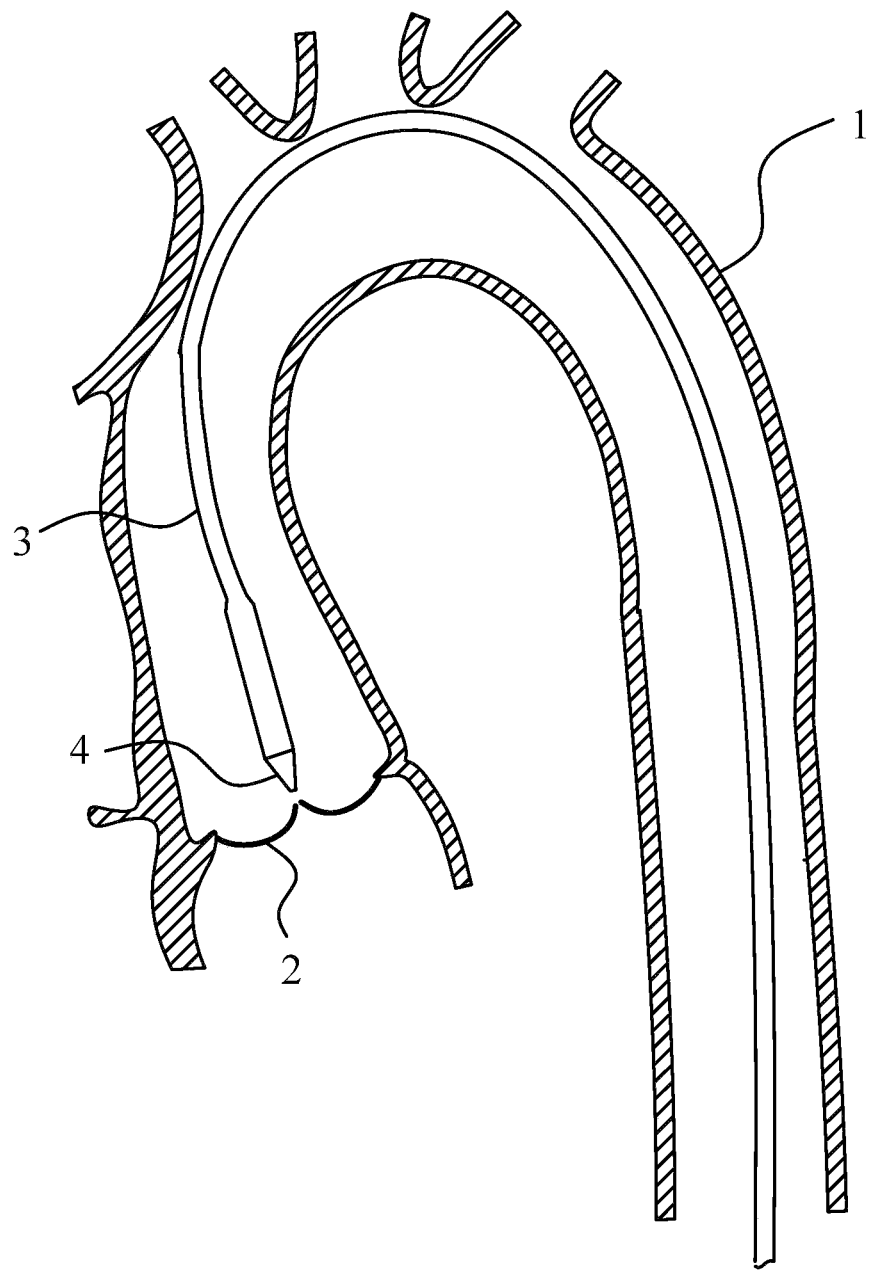
FIG. 1 is a schematic structural diagram of a bendable sheath in an operation configuration in the prior art.

Referring to FIG. 1, an aortic valve replacement in the prior art is shown as an example. An implantable instrument is loaded into a delivery system and enters the aorta 1 under the guidance of the guiding head 4 of the delivery system. After passing through the aortic arch, the implantable instrument advances to a position adjacent to the aortic valve 2. Before being released, the implantable instrument is always surrounded by a tube 3 of the sheath. FIG. 1 shows the position and orientation of the aortic valve 2 with normal physiological structure. The sheath in the prior art can be bent at the distal end thereof and thus the distal end of the delivery system can be bent so that the guiding head 4 can be positioned towards the aortic valve 2.

Figure 2A:
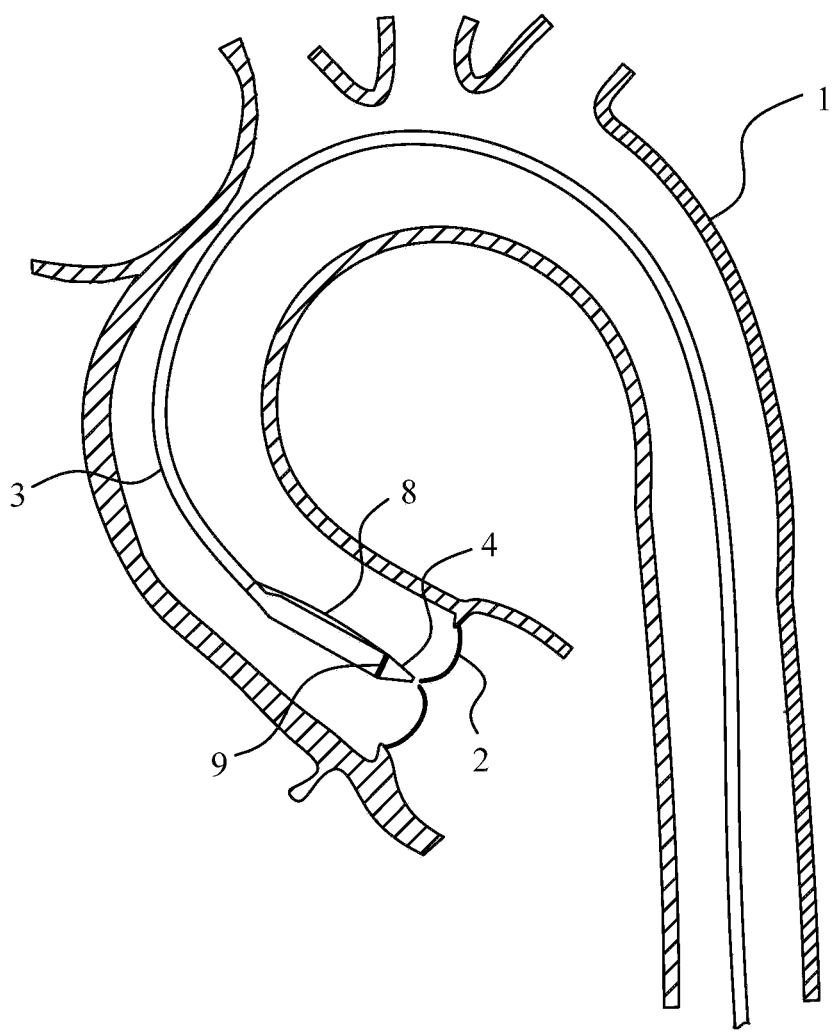
FIG. 2a is a schematic structural diagram of the bendable sheath in an operation configuration of the present disclosure.

Referring to FIG. 2a, due to aortic valve disease, the distal end of the delivery system is required to be bent to a greater extent in some cases. For example, as shown in FIG. 2a, the orientation of the aortic valve 2 has changed, and the distal end of the delivery system has to be bent by almost 270 degrees. In this case, because the stent for the aortic valve located at the distal end has a long length and a greater rigidity, which makes it difficult to be bent, it is difficult to bend the distal end using existing techniques and means. The present disclosure aims at providing a bending technique, based on improvements of the structure, which saves labor, is more convenient, and has a larger adjustable range, without emphasizing the bending degree.

The present disclosure provides a bendable sheath, which may include a tube 3. The tube 3 has a distal end and a proximal end. The tube wall of the tube 3 adjacent to the distal end may be further connected with a pull wire 8. One end of the pull wire 8 may extend towards the proximal end of the tube 3, and the other end is adjacent to the distal end of the tube 3, wherein at least one section of the pull wire 8 is movable outside of the tube 3. In order to improve the connection strength between the pull wire 8 and the tube 3, and to avoid local stress concentration, one end of the pull wire 8 may be provided with a loop 9 which may surround the outer periphery of the tube 3. The tube 3 may be pulled by the entire loop 9. The portion of the tube 3 adjacent to the distal end may be configured as an expandable section for accommodating an implantable instrument. The loop 9 may be located at the distal end of the expandable section.

Referring to FIG. 2a, since the pull wire 8 of the present disclosure has one movable section outside of the tube 3, and the pull wire may be connected to the end of the sheath or less than 3 cm away from the end, the movable section has a greater degree of freedom. The pull wire can be separated from the outer wall of the tube to a certain extent to maintain the existence of some tension, thereby improving the bending degree and the operating experience.

Figure 2B:
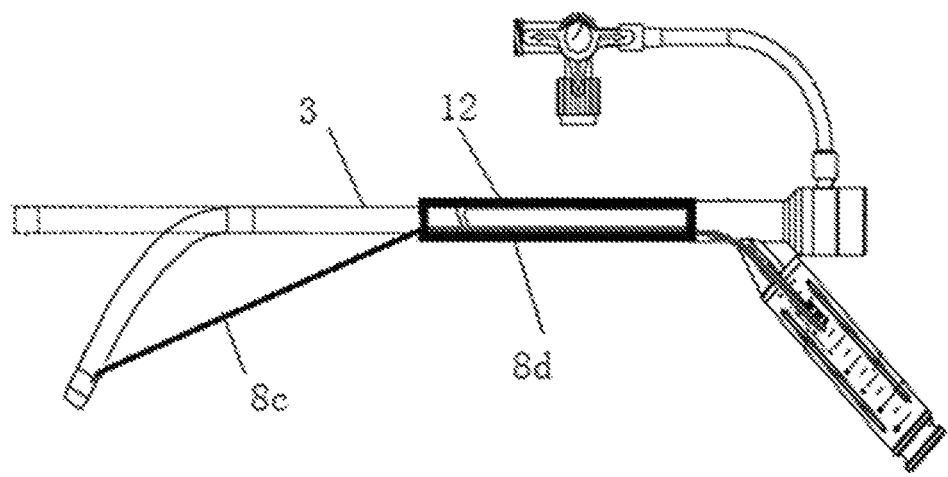
FIG. 2b is a schematic structural diagram of the bendable sheath in another operation configuration of the present disclosure.

Referring to FIG. 2b, the outer wall of the tube 3 in another embodiment may be provided with a sleeve 12. A non-movable section 8d may be provided extending in the gap between the sleeve 12 and the tube 3 until it meets the movable section 8c at the opening of the sleeve 12.

Figure 2C:
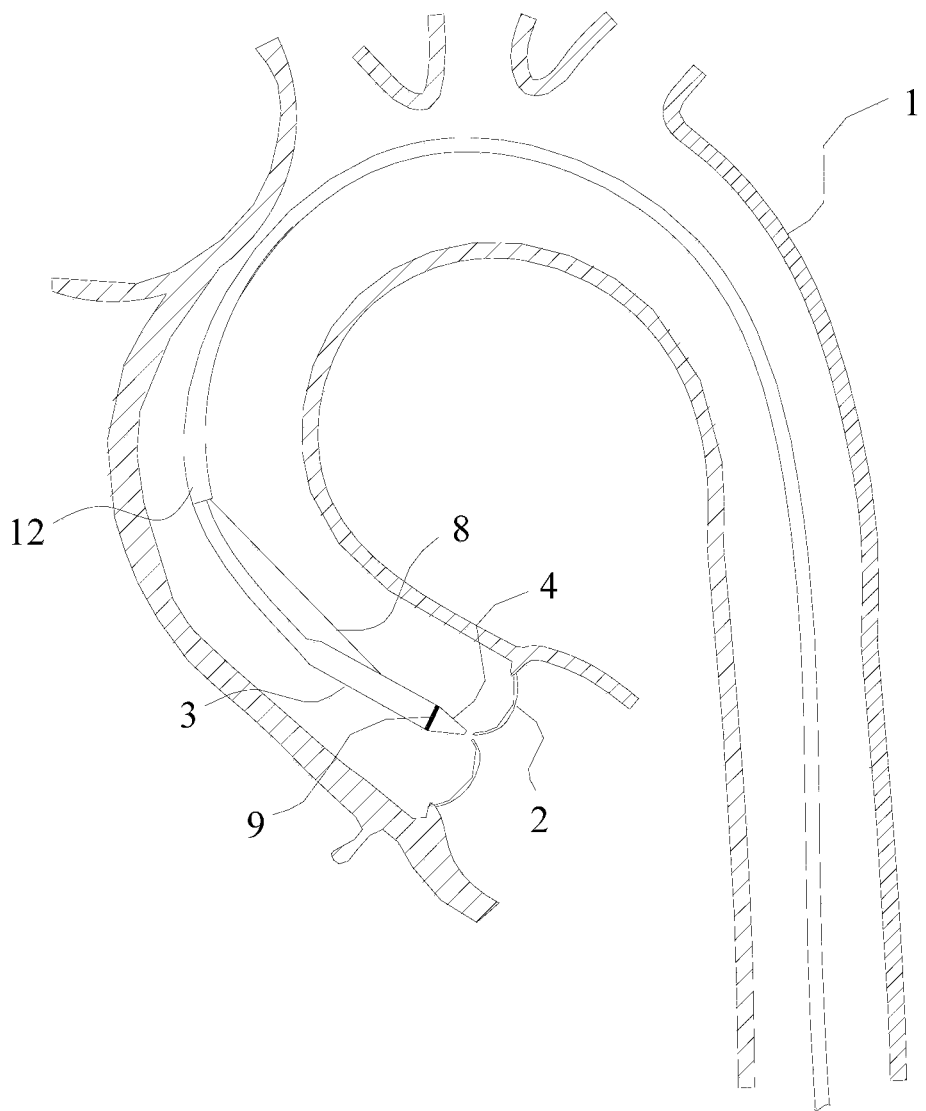
FIG. 2c is a schematic structural diagram of the bendable sheath in another operation configuration of the present disclosure.

Compared with FIG. 2a, the outer wall of the tube 3 in another embodiment as shown in FIG. 2c may be provided with a sleeve 12. One section of the pull wire 8 may extend in the gap between the sleeve 12 and the tube 3 until it meets the movable section at the opening of the sleeve 12. The portion of the tube 3 adjacent to the distal end may be configured as an expandable section for accommodating an implantable instrument. The pull wire 8 may be connected to the middle of the expandable section.

Figure 2D:
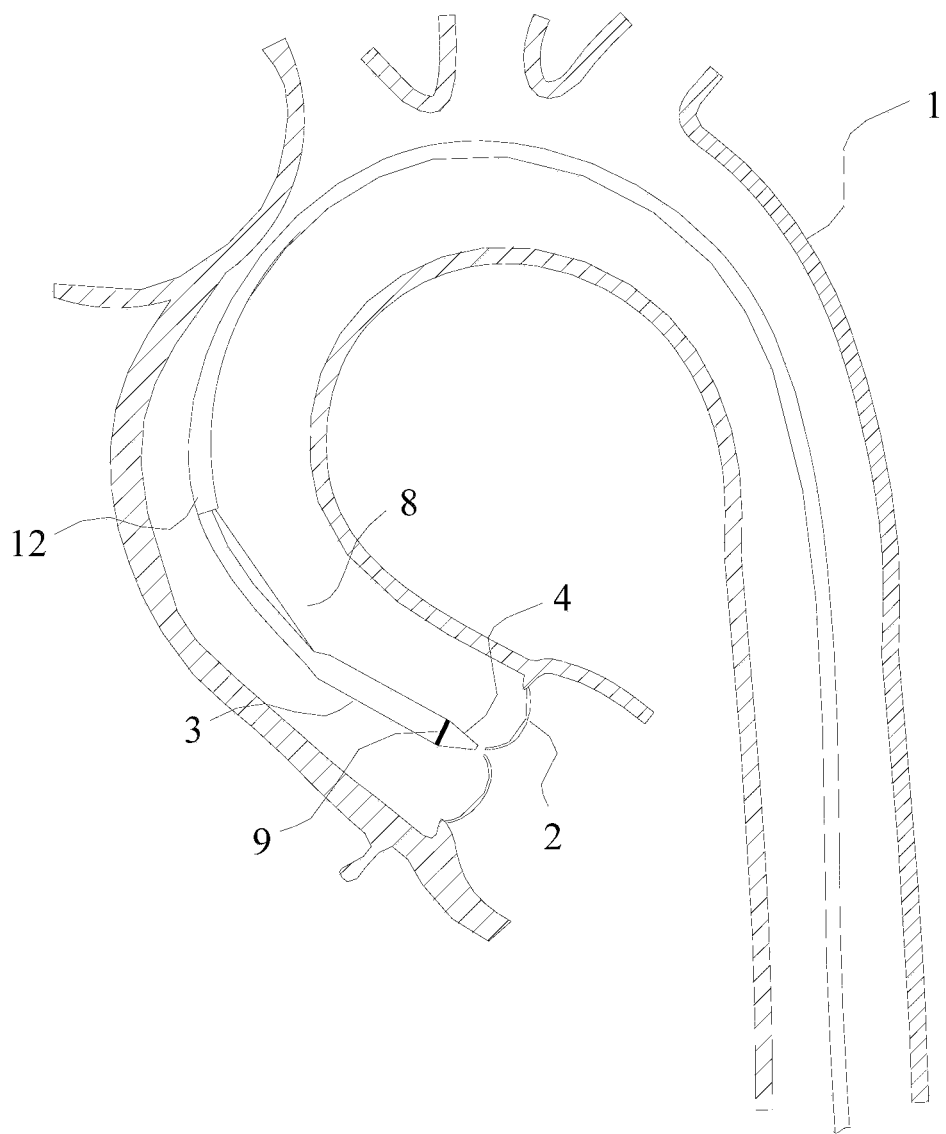
FIG. 2d is a schematic structural diagram of the bendable sheath in another operation configuration of the present disclosure.

Compared with FIG. 2c, the pull wire 8 in another embodiment as shown in FIG. 2d may be connected to the proximal end of the expandable section.

Figure 3:
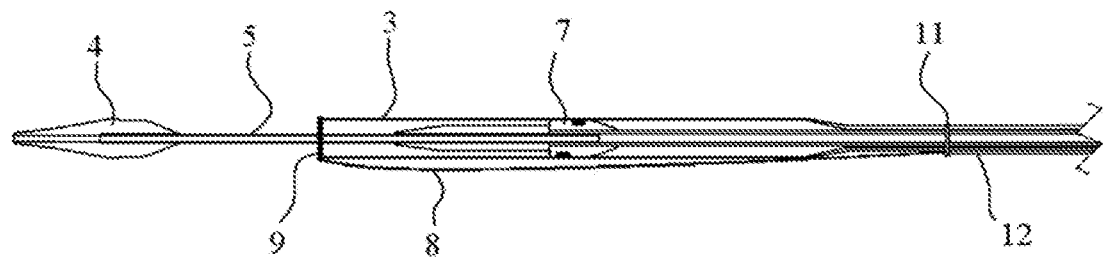
FIG. 3 is a schematic structural view of the distal end of the bendable sheath of the present disclosure.

Referring to FIG. 3, a delivery system of the present disclosure may include a bendable sheath, a sheath core 5 placed in the tube 3 of the bendable sheath, and an operating handle fixed with the proximal ends of the bendable sheath and the sheath core. The proximal end of the pull wire 8 may be connected with the operating handle.

The sheath core 5 may include a core tube on which a guiding head 4 and a fixing head for the implantable instrument 7 may be fixed. The portion of the core tube between the guiding head 4 and the fixing head for the implantable instrument 7 may be used as a loading section for placing the implantable instrument. Before release, the expandable section of the tube 3 surrounds the periphery of the loading section. A sleeve 12 may be provided around the outside of the tube 3. The sleeve 12 may be engaged with and axially slidable relative to the tube 3, and the pull wire 8 may extend towards the proximal end through the gap between the tube 3 and the sleeve 12.

Figure 4:
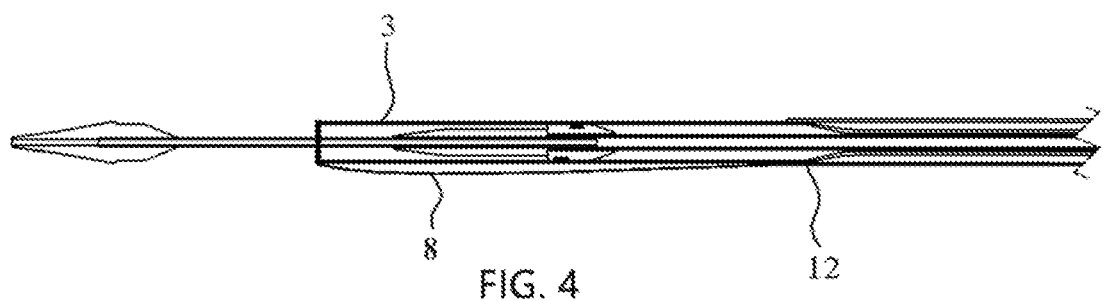
FIG. 4 is a schematic structural diagram of the distal end of the bendable sheath in another embodiment of the present disclosure.
Figure 5:
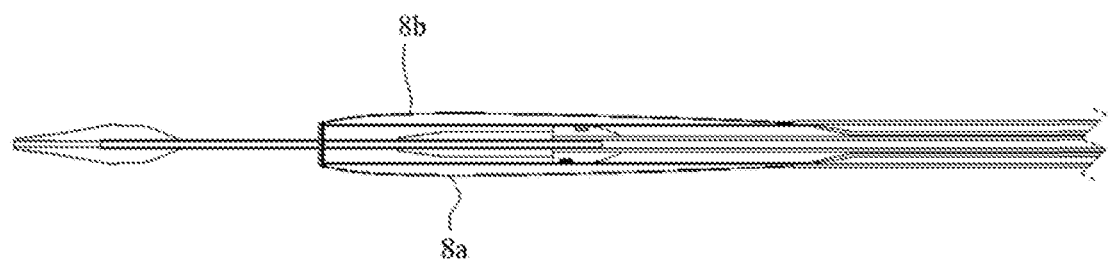
FIG. 5 is a schematic structural diagram of the distal end of the bendable sheath in another embodiment of the present disclosure.

The distal end of the sleeve 12 may be configured as an opening. After the pull wire 8 extends out of the opening, it may be movable outside of the tube 3 until it is connected to the loop 9 at the distal end of the tube 3. In order to improve the strength of the edge of the opening, a reinforcing ring 11 may be provided to prevent the edge of the opening from being locally torn when the pull wire 8 is tensioned. Referring to FIG. 4, in another embodiment, a sleeve 12 may be provided around the outside of the tube 3, and the sleeve 12 may be engaged with and axially slidable relative to the tube 3. The pull wire 8 extends towards the proximal end through the gap between the tube 3 and the sleeve 12. Compared with FIG. 4, two pull wires, namely a pull wire 8a and a pull wire 8b, are provided in another embodiment as shown in FIG. 5. The distal ends of the pull wire 8a and the pull wire 8b may be connected to a loop which may be fixed on the outer wall of the tube or received inside the side wall of the tube.

Figure 6:
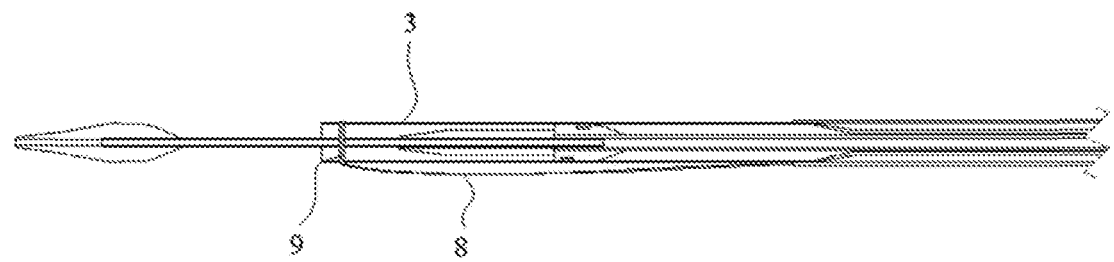
FIG. 6 is a schematic structural diagram of the distal end of the bendable sheath in another embodiment of the present disclosure.

Compared with FIG. 4, the loop 9 in another embodiment as shown in FIG. 6 may be slightly closer to the proximal end to prevent the distal end of the tube 3 from being torn. The width of the loop 9 in the axial direction may be 1~5 mm, and the loop 9 after being unfolded generally presents as a flat strip.

In another embodiment, the loop and the pull wire may be formed in one piece, that is, the distal end of the pull wire itself may be coiled to form a closed ring and then fixed with the pull wire itself.

The loop 9 as shown in FIG. 6 may rotatably surround around the outer wall of the tube 3 and may be limited in the axial direction. The loop 9 may be limited in the axial direction by means of an axial limiting groove or an axial limiting member on the outer wall of the tube.

Figure 7:
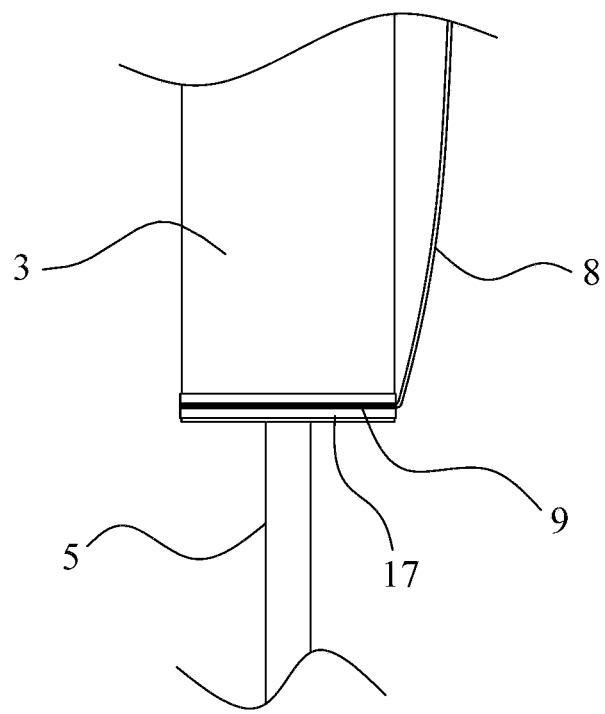
FIG. 7 is a partial schematic diagram of the connection portion of the pull wire and the tube in the bendable sheath of the present disclosure.
Figure 8:
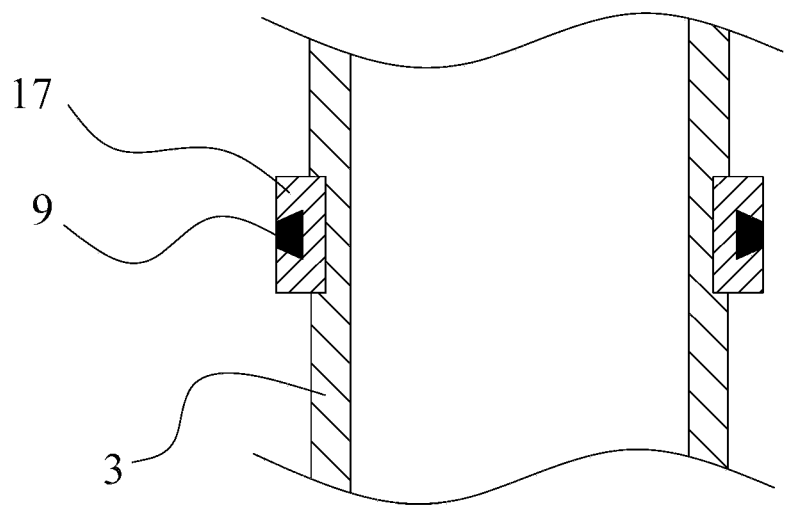
FIG. 8 is a schematic cross-sectional view of the connection portion of the pull wire and the tube in the bendable sheath of the present disclosure.

Referring to FIGS. 7 and 8, the distal end of the tube 3 may be provided with a limiting ring 17. The limiting ring may be a thickened area of the tube 3. Alternatively, the limiting ring may be an annular member that is additionally fixed on the tube 3. The axial limiting groove may be provided on the outer periphery of the limiting ring 17. The loop 9 may be installed in and rotatably engaged with the axial limiting groove. During installation, due to the flexible characteristic of the loop 9, the loop 9 may be simply and directly installed in the axial limiting groove, and the pull wire may be connected to the loop 9. When pulling the pull wire, if the profile of the tube 3 is not ideal, that is, the stressed portion between the pull wire and the loop 9 is not positioned at the inner side of the desired bent section, the loop 9 will be rotated under the stress until the connection portion of the pull wire with the loop 9 rotates to the inner side of the desired bent section. At this time, the pull wire may be further pulled to achieve the desired bending effect.

Figure 9:
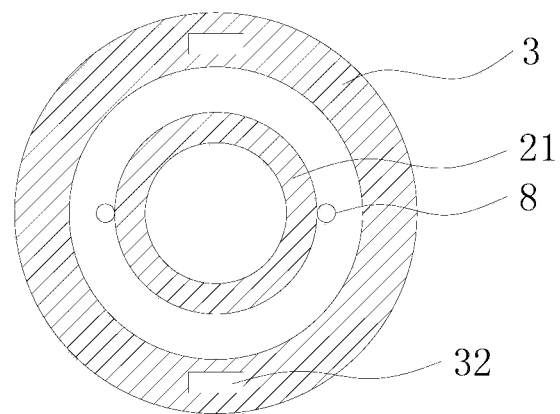
FIG. 9 is a schematic diagram of an arrangement of the pull wires and the reinforcing ribs which are spaced-apart from each other in the bendable sheath of the present disclosure.

Referring to FIG. 9, in another embodiment, in order to further control the profile of the sheath delivered in the human body to cooperate with the bending process, at least one reinforcing rib 32 may be further provided in the side wall of the tube 3.

The reinforcing rib 32 may be directly attached to the inner wall of the tube 3. Alternatively, a channel may be provided in the side wall of the tube 3, and the reinforcing rib 32 may extend in the channel to the distal end. Further, in the case where the reinforcing rib 32 extends in the channel, the reinforcing rib may be movable in the channel, or may be fixed to the wall of the channel.

As shown in the figure, the tube 3 is provided with two reinforcing ribs 32 in the axial direction, and the reinforcing ribs 32 are fixed in the side wall of the tube 3 to improve the possibility of axially pushing the sheath. The two reinforcing ribs 32 in the tube 3 may be arranged opposite to each other, that is, the imaginary connection line of the two reinforcing ribs 32 substantially passes through the axis of the tube 3. In one of the embodiments, two pull wires may be provided, namely the pull wire 8a and the pull wire 8b. In the circumferential direction of the tube 3, two pull wires and two reinforcing ribs 32 may be spaced-apart from each other, and the four may be evenly distributed in the circumferential direction.

The non-movable section of the pull wire extends in the sheath (that is, in the radial gap between the sheath core 21 and the tube 3). The drawings only show the cross section of the pull wire in the sheath.

Figure 10:
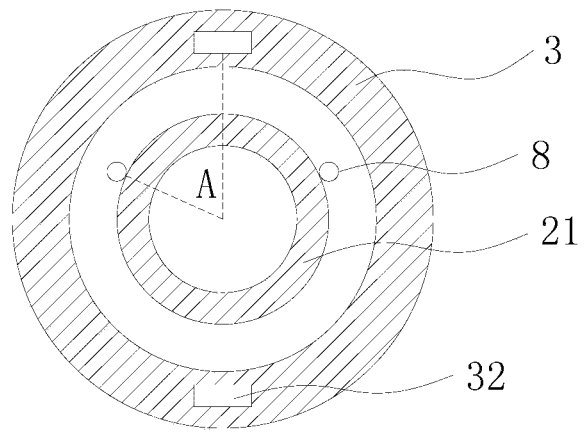
FIG. 10 is a schematic diagram of another arrangement of the pull wires and the reinforcing ribs which are spaced-apart from each other in the bendable sheath of the present disclosure.

As shown in FIG. 10, in one embodiment, both the two pull wires are close to the same reinforcing rib. The central angle A corresponding to the pull wire 8a and the adjacent reinforcing rib is less than 90 degrees, but the central angle A should not be too small to affect the bending process. The central angle corresponding to any reinforcing rib and one of the pull wires on any cross section of the tube should be greater than 30 degrees, usually greater than 60 degrees.

No matter how the pull wire is arranged, it should be spaced-apart from the reinforcing rib 32. Here, since one section of the pull wire is movable, the position of the pull wire may be considered as the position of the connection portion of the pull wire with the tube 3. In the case where the connection portion of the pull wire with the tube 3 is changeable, for example, in the case where the pull wire is connected with the tube 3 by means of the rotatable loop, the position of the pull wire may be considered as the position to which the pull wire adaptively moves when it is tensioned.

When the delivery system is required to be bent, an operator may pull the pull wire, and the pulling force from the pull wire can drive the distal end of the tube 3 to bend. The two reinforcing ribs 32, which are arranged opposite to each other in the tube wall of the sheath, enhance the radial force of the tube 3. The cross section of the reinforcing rib 32 may be shaped as a strip of material. The tube 3 cannot be bent in the longitudinal direction of cross section of the reinforcing rib, but can only be bent in the thickness direction of the reinforcing rib 32. In other words, the bending direction of the tube 3 is limited. Because the pull wire and the reinforcing rib 32 are spaced-apart from each other in the circumferential direction, when the pull wire is pulled, the distal end of the sheath can be inevitably and easily bent towards the pull wire. The distal end of the sheath can be more easily bent in the target direction through pulling and rotating operations.

Alternatively, the two reinforcing ribs 32 may not be arranged opposite to each other. The central angle corresponding to the two reinforcing ribs 32 on any cross section of the tube 3 may be less than 180 degrees. However, it should be noted that, because the sheath should not be bent in the radial direction between each reinforcing rib 32 and the axis of the tube 3, it is necessary to avoid the pull wire being distributed on the radial line between any reinforcing rib 32 and the axis of the tube 3.

In another embodiment, one section of the pull wire adjacent to the distal end may be configured as an imaging section. The imaging section may be made of materials containing developable components, or may be provided in the form of a built-in material, external coating, covering, or the like, provided that it can be observed by a medical imaging system.

Since one section of the pull wire is configured as a movable section outside of the tube, in a bent configuration, the course of extension experienced by the movable section is different from that of the tube 3. Therefore, in order to avoid misjudgment of the profile of the tube 3, the length of the imaging section may be larger than that of the movable section.

Referring to the general length of the sheath, the length of the imaging section may be configured to be greater than 12 cm.

It is easy to understand that the longer the length of the imaging section of the pull wire, the more advantageous it would be to indicate the turning position to determine the approximate turning angle and direction during bending the sheath. Therefore, the imaging section may be configured to form a developing area that is continuously distributed and thereby forming a continuous indication route. In another embodiment, the imaging section may be configured to form a plurality of developing points that are spaced-apart from each other, and the extension direction of the tube 3 may be roughly determined by the spaced developing points.

Figure 11:
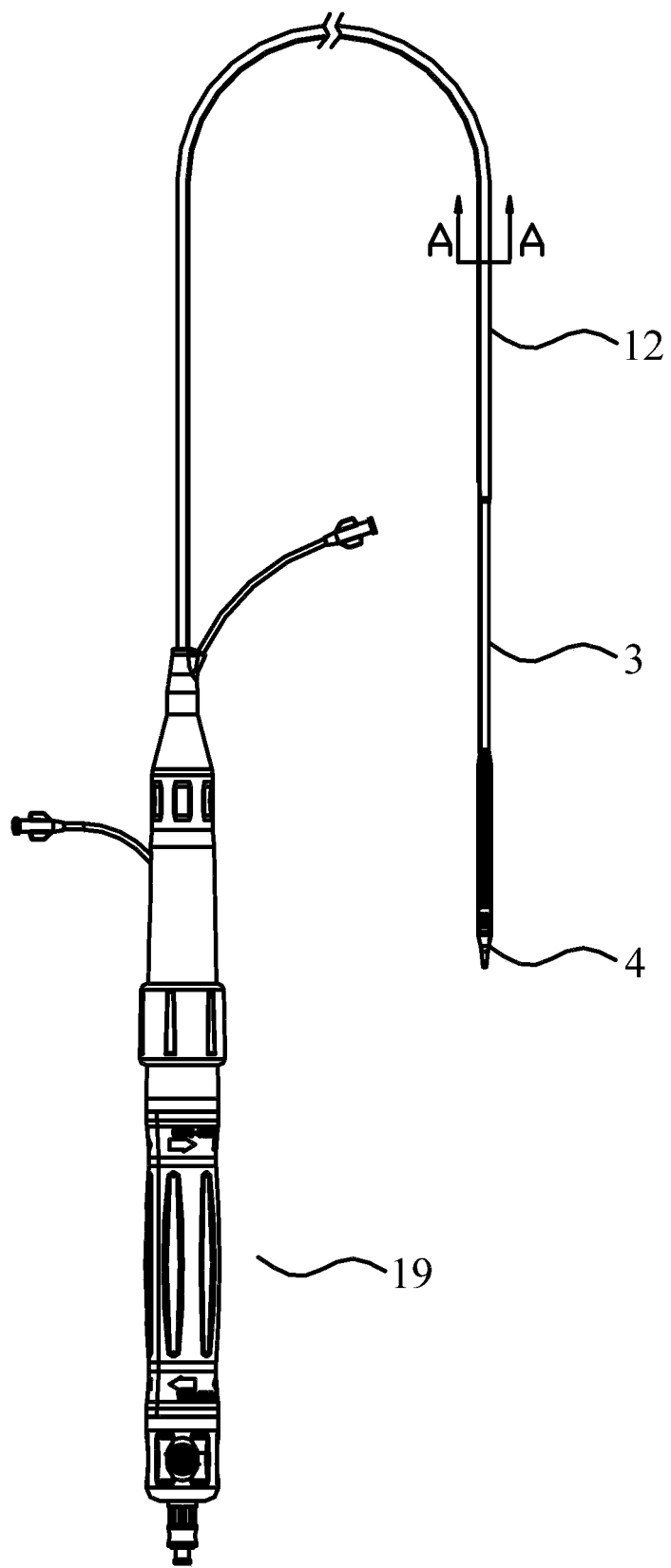
FIG. 11 is a schematic structural diagram of the bendable delivery system for an implantable valve of the present disclosure.
Figure 12:
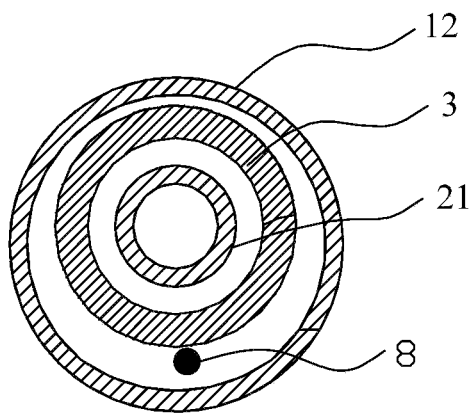
FIG. 12 is a cross-sectional view taken along A-A of FIG. 11.

Referring to FIG. 11 and FIG. 12, the delivery system of the present disclosure may be further provided with an operating handle 19. A sleeve 12 may be slidably provided on the outside of the tube 3 of the bendable sheath. A sheath core 21 may be provided inside the tube 3, and the distal end of the sheath core 21 may extend out of the tube 3 and may be provided with a guiding head 4.

The pull wire 8 moveably extends with one distal section thereof, and then enters the gap between the sleeve 12 and the tube 3, and extends towards the proximal end to the operating handle.

Figure 13:
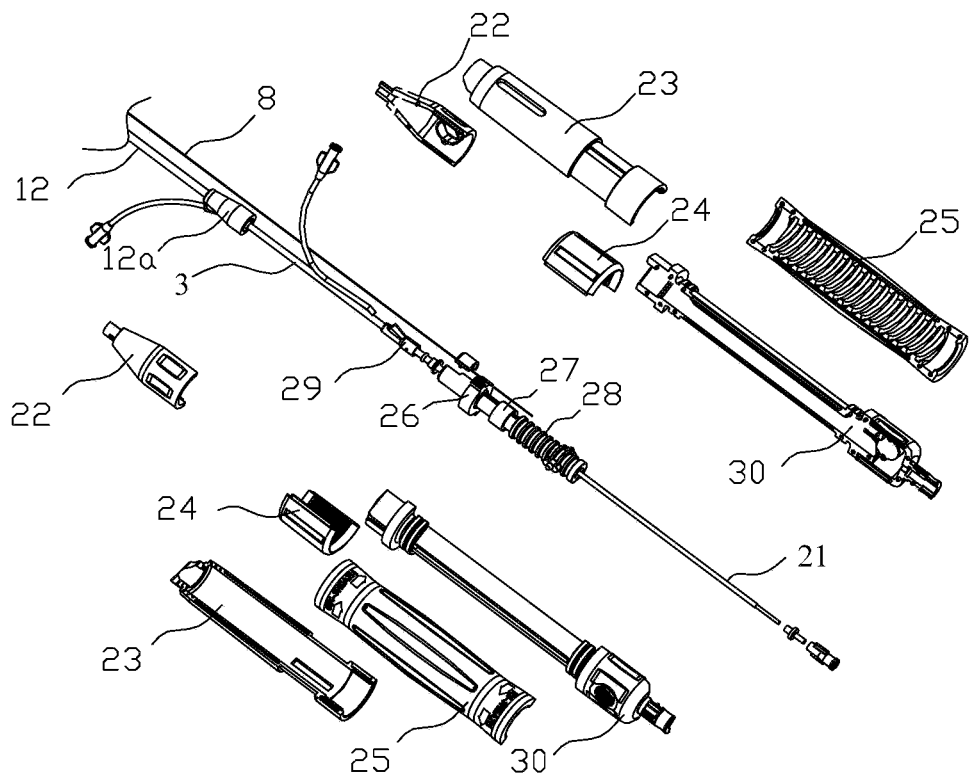
FIG. 13 is an exploded view of the operating handle of the bendable delivery system for the implantable valve of FIG. 11.
Figure 14:
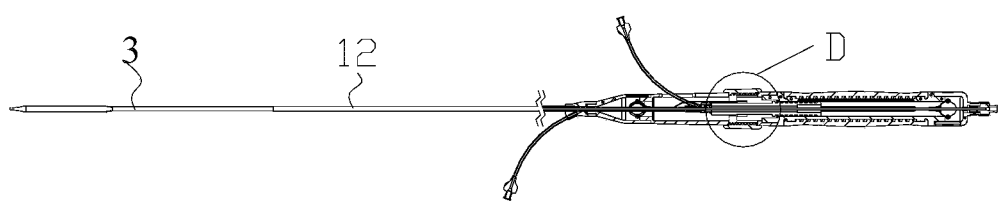
FIG. 14 is a schematic structural diagram of the bendable delivery system for the implantable valve of FIG. 11 shown before bending.
Figure 15:
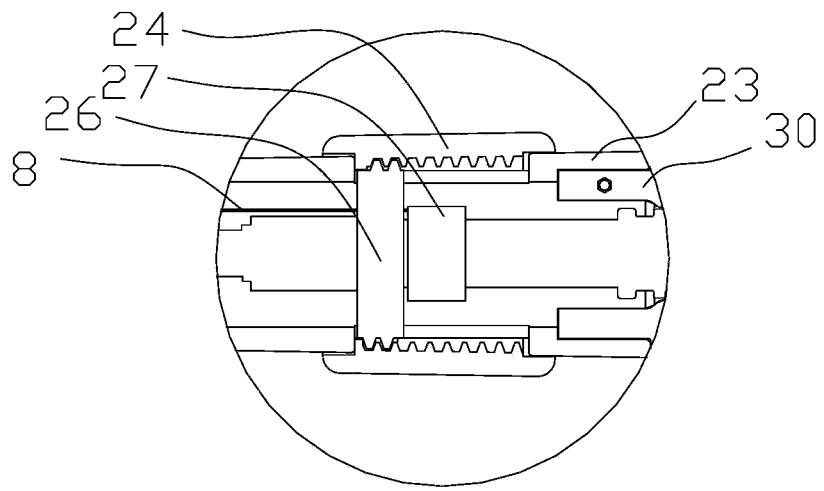
FIG. 15 is an enlarged view of part D of FIG. 14.

Referring to FIG. 13, the operating handle may include a fixed body 30 with a hollow structure. The fixed body 30 may be configured as a detachable structure including two engageable parts. The fixed body 30 has a hollow structure. Both the tube 3 and the sheath core 21 may pass through the inside of the fixed body 30.

The side wall of the fixed body 30 may be provided with a hollow guiding groove. A transmission rod 28 may be slidably installed in the fixed body 30, and the outer wall of the transmission rod 28 may be fixed with linkage teeth. The linkage teeth may extend out of the guiding groove. A control handle 25 may rotatably surround the fixed body 30. The control handle 25 may be configured as a detachable structure including two engageable parts. The control handle 25 may have internal threads inside which cooperate with the linkage teeth. When the control handle 25 is rotated, the transmission rod 28 can be driven to move axially, and the tube 3, which may be connected to the transmission rod 28 through a sheath connector, can then be driven by the transmission rod 28.

The transmission rod 28 may also have a hollow structure in the axial direction. The sheath core 21 may pass through this hollow structure, and may extend to and be connected to the proximal portion of the fixed body 30. A front handle 23 may be fixed at the distal end of the fixed body 30. A front cap 22 may be installed at the distal end of the front handle 23. The proximal end of the sleeve 12 may be connected to a slidable seat 12a which may be inserted into and movably engaged with the front cap 22. Both the front handle 23 and the front cap 22 may be configured as detachable structures including two engageable parts.

A pulling member 27 and a movable member 26 may be provided around and slidably engaged with the outside of the transmission rod 28, wherein the pulling member 27 may be connected to the pull wire 8, and the movable member 26 may be attached to the distal end of the pulling member. The front handle 23 may be provided with a hollow axial guiding groove. A part of the movable member 26 may extend out of the axial guiding groove, which may be provided with external threads. An adjustable knob 24 may be rotatably installed in the front handle 23. The adjustable knob 24 may be configured as a detachable structure including two engageable parts. The inner wall of the adjustable knob 24 may be provided with internal threads that engage with the external threads of the movable member 26.

Figure 16:
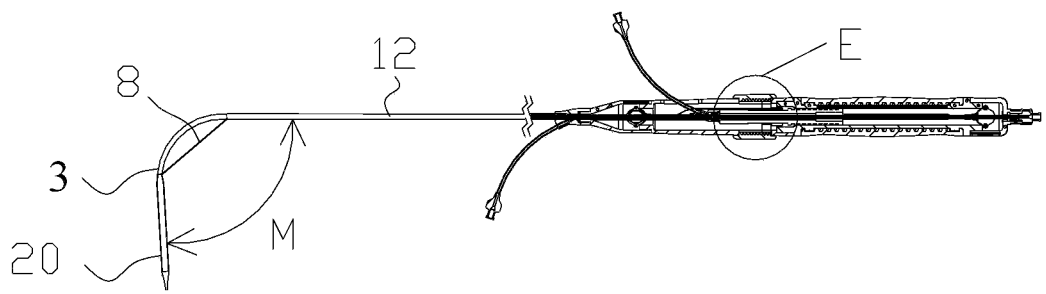
FIG. 16 is a schematic structural diagram of the bendable delivery system for the implantable valve of FIG. 11 shown after bending.
Figure 17:
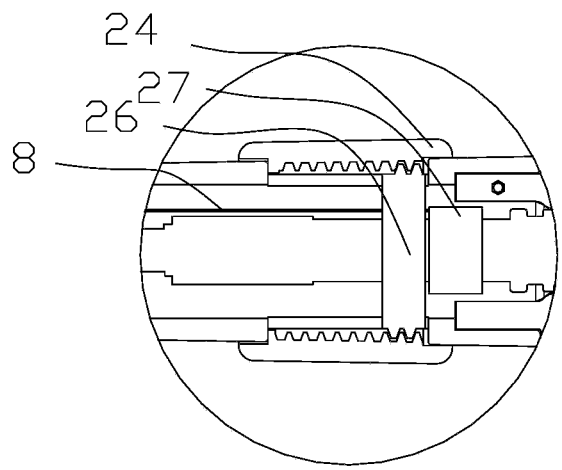
FIG. 17 is an enlarged view of part E of FIG. 16.
Figure 18:
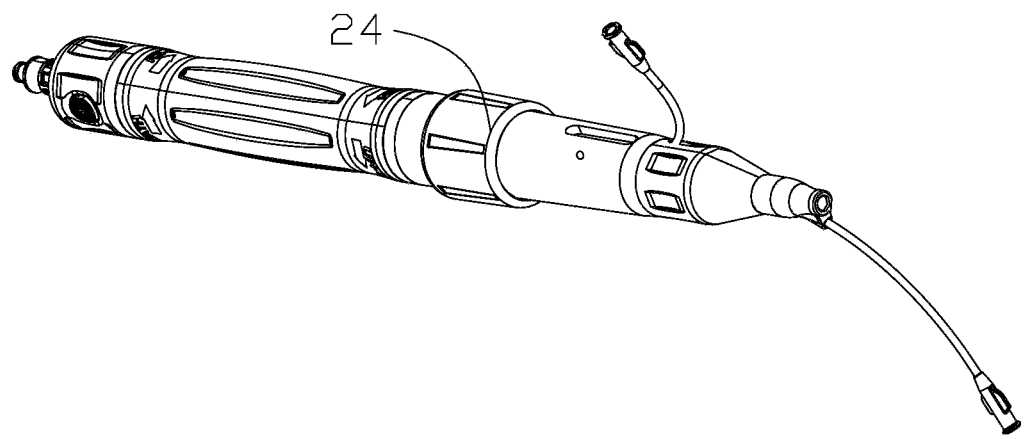
FIG. 18 is a perspective view of the operating handle of the bendable delivery system for the implantable valve of FIG. 11.
Figure 19:
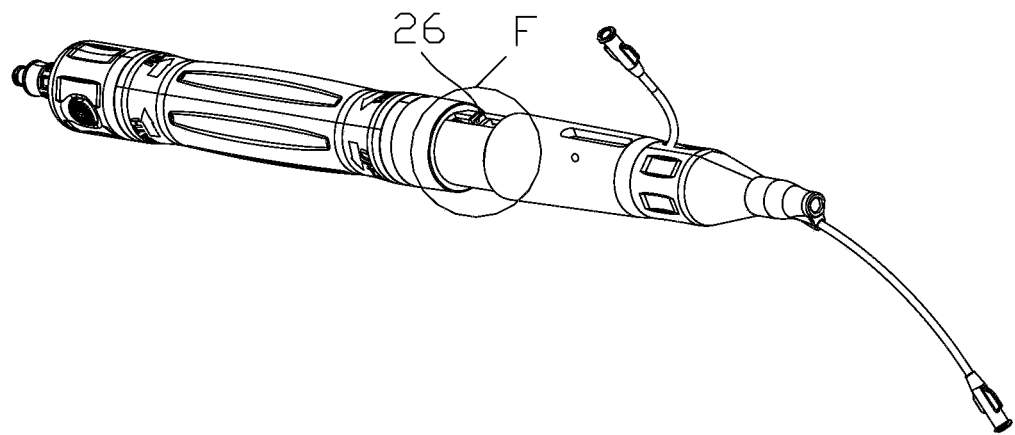
FIG. 19 is a schematic diagram of FIG. 18 with the adjustment knob not shown.
Figure 20:
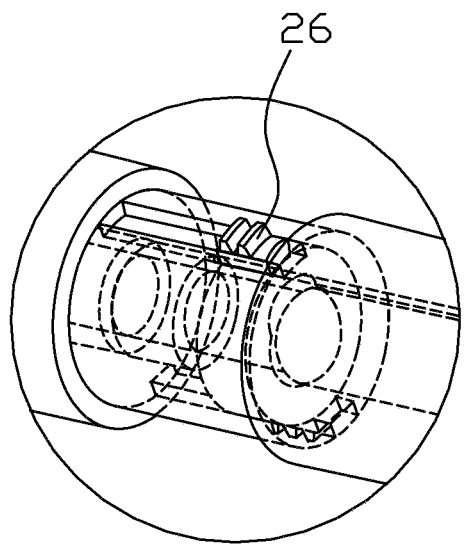
FIG. 20 is an enlarged view of part F of FIG. 19.

Referring to FIGS. 14 to 20, when the sheath needs to be bent, an operator may rotate the adjustable knob 24, and thus the movable member 26 can be driven to move axially, and then the pull wire 8 can be driven through the pulling member 27. The distal end of the tube 3 may be driven by the pull wire 8 into the bent configuration as shown in FIG. 16. The angle M may range from 52 degrees to 180 degrees, and the axial traveling distance of the pulling member 27 may range from 1 mm to 30 mm. When the pulling member 27 moves the maximum traveling distance, the angle M becomes the smallest. During bending of the sheath, a section of the pull wire 8 adjacent to the distal end may be configured as the imaging section to indicate the turning portion. The length of the imaging section may be 12 cm to 20 cm, and for example, 15 cm. In the unbent configuration, at least one part of the imaging section at the proximal end extends into the sleeve, so that a slight bent sheath can also be observed through the medical imaging system.

After the implantable instrument is delivered to the predetermined position, the sheath may be withdrawn through the control handle 25. During withdrawal of the sheath, the implantable instrument is gradually released. In the initial stage of release, if the profile or position of the implantable instrument needs to be adjusted, the sheath can be pushed forward to re-cover the implantable instrument, i.e., to retrieve the implantable instrument. The closer to the end stage of the release, the more difficult it would be to retrieve the implantable instrument.

After the operator starts releasing the implantable instrument, the movable section of the pull wire will gradually become slack with the withdrawal of the tube 3. The force from the slack movable section to the tube 3 will be reduced, and the bending angle will change accordingly, causing the position of the expandable section of the tube 3 being initially bent to be changed. A limiting member may be provided to prompt the operator to adjust the tightness of the pull wire while the implantable instrument is still retrievable during the release process, so as to drive the sheath back to the previous bent configuration and maintain the position and profile of the implantable instrument.

Figure 21:
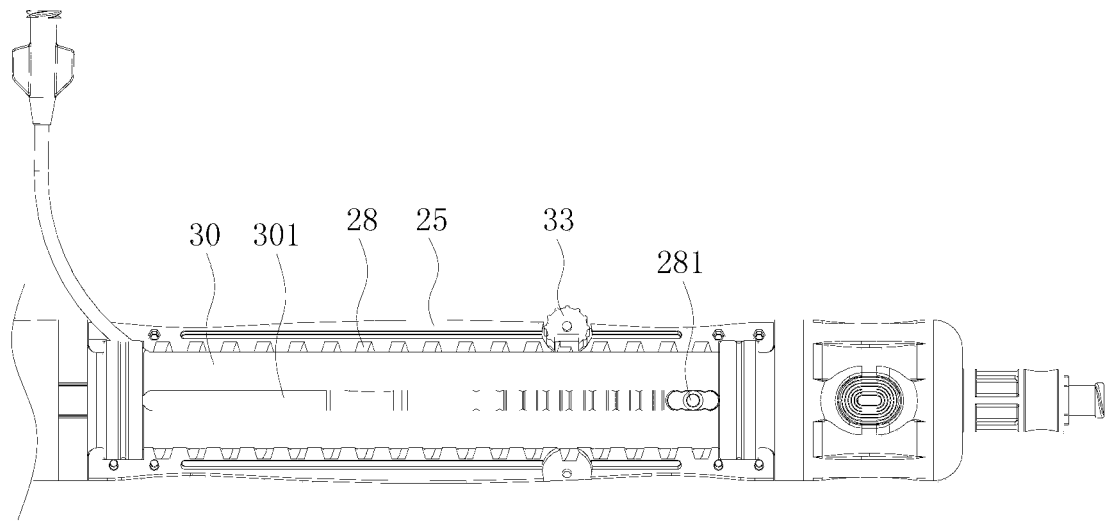
FIG. 21 is a schematic structural view of the operating handle in the bendable sheath of the present disclosure with half of the control handle not shown.

Referring to FIG. 21, in another embodiment, the control handle 25 may be provided with a limiting member that limits the axial displacement of the transmission rod 28. It can be seen from the foregoing that the transmission rod 28 may be connected to the tube 3 through the sheath connector, which means that limiting the axial displacement of the transmission rod 28 will also limit the withdrawal displacement of the tube 3, so as to prompt the operator to further confirm the profile or position of the implantable instrument during the release.

In order to allow subsequent withdrawal of the tube 3, the limiting member may be movably mounted on the control handle 25. The limiting member has a limiting configuration where the limiting member abuts against the linkage teeth 281, and a release configuration where the limiting member avoids the linkage teeth 281.

When the limiting member assumes the limiting configuration, the limiting member may block the movement path of the linkage teeth 281 along the guiding groove 301 of the fixed body 30 to prevent the transmission rod 28 from driving the tube 3 to withdraw. When the limiting member assumes the release configuration, the limiting member may avoid the movement path of the linkage teeth 281 along the guiding groove 301 of the fixed body 30 to allow the transmission rod 28 to continue driving the tube 3 to withdraw until the stent is released.

In another embodiment, the transmission rod 28 may be provided with two sets of linkage teeth 281 that are arranged opposite to each other. In order to achieve the optimal limiting effect, the control handle 25 may be also provided with two limiting members that are arranged opposite to each other.

The limiting member should rotate with the control handle 25, and also pass through the side wall of the control handle 25 to engage with the linkage teeth 281. In order to facilitate the installation of the movable limiting member, an installation opening may be provided on the side wall of the control handle 25. The limiting member may be movably received in the installation opening.

Figure 22:
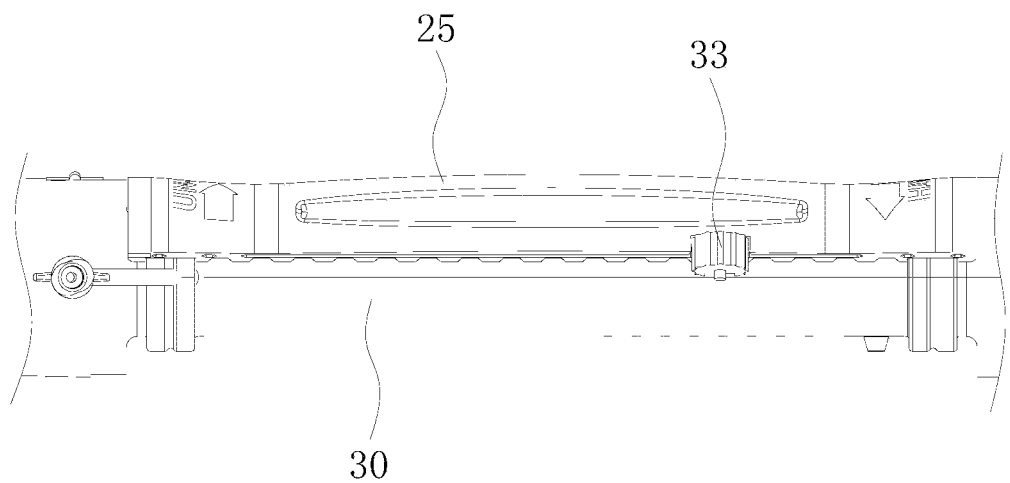
FIG. 22 is a top view of FIG. 21.

As shown in FIG. 22, in one embodiment, a pivot may be provided at the installation opening of the control handle 25, and the limiting member may be configured as an adjustable wheel 33 which is mounted on the pivot and rotatable. The adjustable wheel 33 may be in a tight fit with the pivot and does not rotate without external force. When a certain external force is applied, the adjustable wheel 33 can rotate at a specified angle.

The adjustable wheel 33 can be driven to rotate by directly applying an external force to the adjustable wheel 33, or by a transmission component. In order to simplify the structure of the control handle 25, at least a part of the outer periphery of the adjustable wheel 33 may be arranged outside the installation opening, so as to directly apply a rotating force to the adjustable wheel 33.

Further, in another embodiment, the exposed portion of the adjustable wheel 33 may be provided with an anti-slip structure to avoid slippage during the rotation of the adjustable wheel 33. The anti-slip structure may be configured as ridges, grooves, or the like provided on the adjustable wheel 33. Alternatively, an anti-slip material, such as an anti-slip mat, may be added to the adjustable wheel 33 in the form of a built-in material, coating, or covering.

Since the adjustable wheel 33 translates between the limiting configuration and the release configuration by rotation, the part of the adjustable wheel 33 outside the installation opening is changeable relative to the entire adjustable wheel 33. In other words, the exposed portion refers to the portion of the adjustable wheel 33 outside the installation opening, and the exposed portion may be provided with an anti-slip structure.

Figure 23:
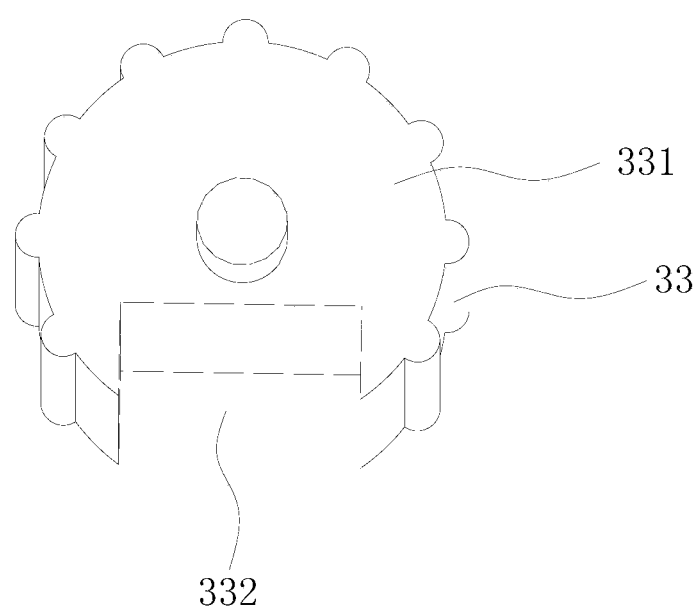
FIG. 23 is a schematic structural diagram of the adjustable wheel in the bendable sheath of the present disclosure.

Referring to FIG. 23, the axial end surface of the adjustable wheel 33 may serve as a limiting surface 331. In the limiting configuration, the limiting surface 331 blocks the movement path of the linkage teeth 281. The outer periphery of the adjustable wheel 33 may be provided with an avoidance groove 332. In the release configuration, the avoidance groove 332 corresponds to the movement path of the linkage teeth 281, and the linkage teeth 281 are allowed to pass through the avoidance groove 332 to continue the movement.

The rotation of the adjustable wheel 33 changes the position of the avoidance groove 332 or the position of the limiting surface 331. Since both the avoidance groove 332 and the linkage teeth 281 have a certain width, the linkage teeth 281 is only allowed to pass through the avoidance groove 332 when the avoidance groove 332 is in proper alignment. In another embodiment, in order to quickly determine the proper position of the avoidance groove 281, a mark may be provided on the adjustable wheel 33, which can indicate the configuration of the limiting member, so as to allow the adjustable wheel 33 to quickly move between the limiting configuration and the release configuration.

Figure 24:
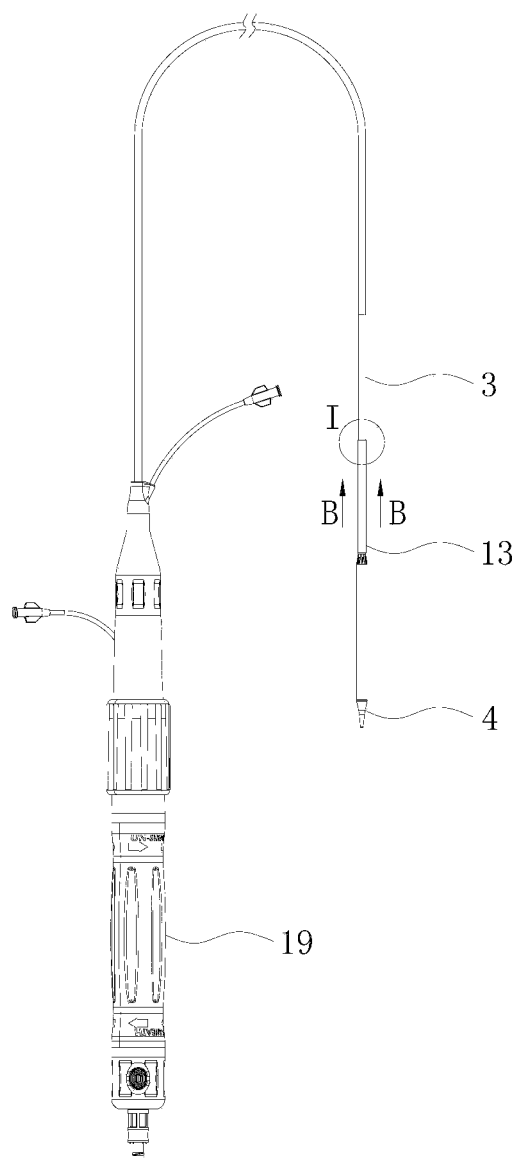
FIG. 24 is a schematic structural diagram of the bendable delivery system for an implantable valve of the present disclosure with a guiding member added.
Figure 25:
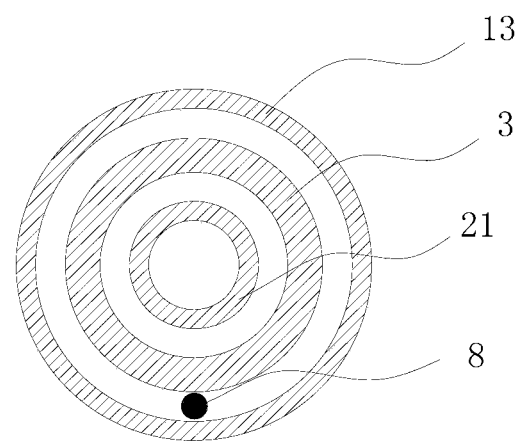
FIG. 25 is a cross-sectional view taken along B-B of FIG. 24.

Referring to FIGS. 24 and 25, in another embodiment, in order to prevent the movable section of the pull wire 8 from cutting the aorta and to improve safety, the bendable sheath in the present disclosure may be further provided with a guiding member 13 acting between the tube 3 and the movable section, which functions to delimit the gap between the tube 3 and the movable section during bending.

The guiding member 13 acting between the tube 3 and the movable section means that the guiding member 13 applies a force on both.

The movable section, as a part of the pull wire 8, is located outside the tube 3, and a gap will be formed between the movable section and the tube 3 in the radial direction during bending. After a force is applied to the movable section, the radial gap between the movable section and the tube 3 will change, and the tensioning can be maintained to obtain an ideal bending profile. The guiding member delimits the gap between the tube 3 and the movable section provided that it would not cause adverse effects on the pulling of the tube 3.

Figure 26:
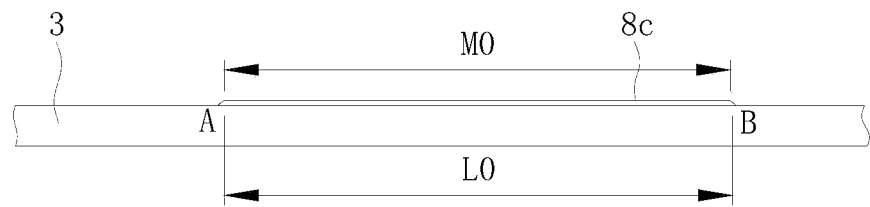
FIG. 26 is a schematic structural diagram of the movable section and the tube in the bendable sheath of the present disclosure shown before bending.

Referring to FIG. 26, the distance between a point A and a point B on the tube 3 is designated as $L_0$, and the pulling wire 8 passes through the tube 3 at the two points A and B to form the movable section 8c of length $M_0$. At this time, both the movable section 8c and the tube 3 assume the original configurations, and $L_0 \approx M_0$.

Figure 27:
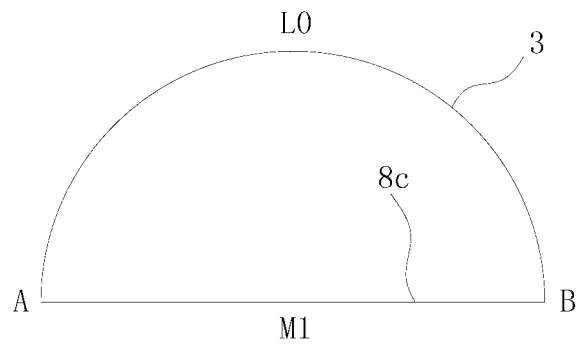
FIG. 27 is a schematic structural diagram of the movable section and the tube in the bendable sheath of the present disclosure shown after bending.

Referring to FIG. 27, in order to simply show the bent configuration of the tube 3 and to facilitate subsequent description, the thickness of the tube 3 is not shown in the figure.

It can be seen from the figure that when the movable section 8c is tensioned, the AB section of the tube 3 is driven to bend. Assuming that the arc formed by the bent AB section of the tube 3 is a semicircle, the shortened distance of the movable section relative to the initial length thereof can be calculated according to the formula of the circumference: $C = 2\pi r$.

The calculation process is as follows: since the chord facing the semicircle is the diameter, the line section AB is the diameter; the length of the line section AB is $M_1$, then $$L_0 = \pi \frac{M_1}{2}, \quad M_1 = \frac{2L_0}{\pi} \approx 0.64 L_0$$

may be obtained.

The shortened distance of the movable section 8c can be obtained, that is $M_0 - M_1 \approx L_0 - 0.64 L_0 = 0.36 L_0$.

It can be seen that when the tube needs to be bent such that the arc formed by the bent AB section of the tube presents as a semicircle, the shortened distance of the movable section 8c by pulling is $0.36 L_0$. In other words, the length of the pulling wire 8 to be pulled at the operating handle is $0.36 L_0$.

Figure 28:
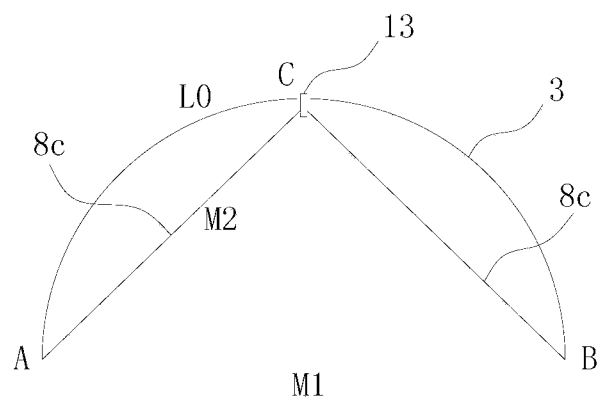
FIG. 28 is a schematic structural diagram of the movable section and the tube of the bendable sheath of the present disclosure shown after bending with a guiding member added.

Compared with FIG. 27, the guiding member 13 as shown in FIG. 28 is provided between the movable section 8c and the tube 3. For the convenience of calculation, the guiding member 13 may be provided at a point C where the center line of the line section AB intersects with the arc AB.

For the convenience of calculation, the thickness of the tube 3 is not shown in this figure either. Also assumed is that the central angle corresponding to the arc AB is 180 degrees and the length of the arc AB is $L_0$, and the line section AB is also the diameter of the circle where the arc AB is located, and the length of the line section AB is $M_1$.

The guiding member 13 delimits the gap between the movable section 8c and the tube 3, so that the radial gap between the two maintains narrow, and the movable section 8c forms a line section ACB under the constraint of the guiding member 13. In order to facilitate the calculation of the shortened distance of the movable section 8c, it may be assumed that at the point C, the movable section 8c is very close to the tube 3.

Then $\triangle ABC$ is configured as an inscribed triangle, $\angle ACB = 90°$, and the length of the line section AC is equal to the length of the line section CB.

Therefore, the length of the movable section 8c under tension can be obtained as follows:

$$M_2 = 2 \times \frac{M_1}{\sqrt{2}} \approx 1.41 M_1.$$

As the foregoing has proven that $M_1 \approx 0.64 L_0$, then $M_2 \approx 1.41 M_1 = 1.41 \times 0.64 L_0 \approx 0.90 L_0$.

It can be obtained that, under the action of the guiding member 13, the shortened distance of the movable section 8c is $M_0 - M_2 \approx L_0 - 0.90 L_0 = 0.10 L_0$.

It can be seen that when the tube needs to be bent such that the arc formed by the bent section AB of the tube presents as a semicircle, the shortened distance of the movable section 8c by pulling is $0.10 L_0$. In other words, the length of the pulling wire 8 to be pulled at the operating handle is $0.10 L_0$.

It can be seen from the comparison between the calculation result according to FIG. 27 and the calculation result according to FIG. 28, provided that the AB section of the tube 3 is driven to bend to the same arc, the shortened distance of the movable section 8c is smaller in the case where the guiding member 13 is provided; that is, the length of the pull wire 8 pulled by the operating handle is smaller, which not only facilitates the bending operation, but also further improves the bending sensitivity and the bending effect.

Figure 29:
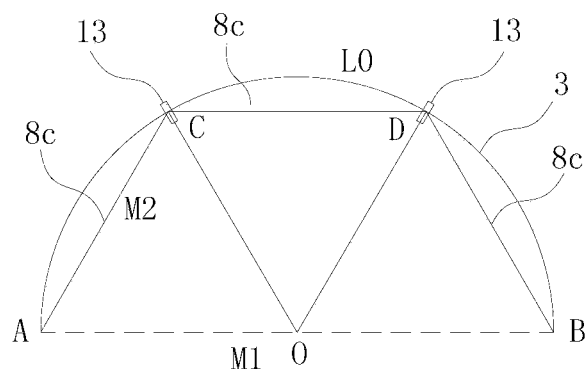
FIG. 29 is another schematic structural diagram of the movable section and the tube of the bendable sheath of the present disclosure shown after bending with a guiding member added.

Further, referring to FIG. 29, two guiding members 13 are provided between the movable section 8c and the tube 3. Again, the central angle corresponding to the arc AB is 180 degrees, and the length of the arc AB is $L_0$, the line section AB is also the diameter of the circle where the arc AB is located, and the length of the line section AB is $M_1$.

For the convenience of calculation, the thickness of the tube 3 is not shown in this figure either, and it is assumed that at points C and D, the movable section 8c is very close to the tube 3. The guiding members 13 at the points C and D are arranged at the positions such that equilateral triangles $\triangle ACO$, $\triangle COD$, and $\triangle O3D$ are formed, and the point O is the center of the circle where the arc AB is located.

Based on the above assumptions, it can be obtained that the length $M_2$ of the movable section 8c is $$M_2 = \frac{3M_1}{2}$$

in the case where the movable section 8c is limited by the two guiding members 13.

As the foregoing has proven that $M_1 \leq 0.64L_0$, then $M_2 - 1.5M_1 \approx 1.5 \times 0.64L_0 \approx 0.96L_0$.

It can be obtained that, under the action of the two guiding members 13, the shortened distance of the movable section 8c is $M_0 - M_2 \approx L_0 - 0.96L_0 = 0.04L_0$.

It can be seen that when the tube needs to be bent such that the arc formed by the bent AB section of the tube presents as a semicircle, the shortened distance of the movable section 8c by pulling is $0.04L_0$. In other words, the length of the pull wire 8 to be pulled at the operating handle is $0.04L_0$.

Compared with the calculation results according to FIG. 27 and FIG. 28, provided that the AB section of the tube 3 as shown in FIG. 29 is driven to bend to the same arc, the shortened distance of the movable section 8c is smaller in the case where the guiding members 13 are provided, that is, the length of the pull wire 8 pulled by the operating handle is smaller.

It can be concluded from FIGS. 27 to 29 that, in the case where a guiding member 13 is provided between the movable section 8c and the tube 3, the pulled distance of the pull wire 8 becomes smaller provided that the tube 3 is bent to the same degree. The greater the number of the provided guiding members 13, the smaller the pulled distance of the pull wire 8.

Figure 30:
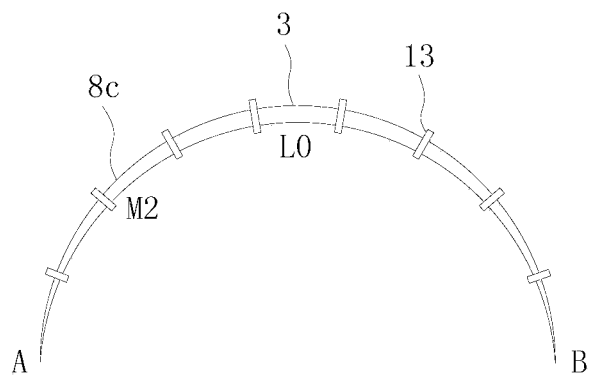
FIG. 30 is another schematic structural diagram of the movable section and the tube of the bendable sheath of the present disclosure shown after bending with a guiding member added.

Referring to FIG. 30, it can be seen that the greater the number of the guiding members 13 provided between the movable section 8c and the tube 3, the stronger the guiding members 13 constrain the extension of the movable section 8c, that is, the better the bending sensitivity is.

Figure 31:
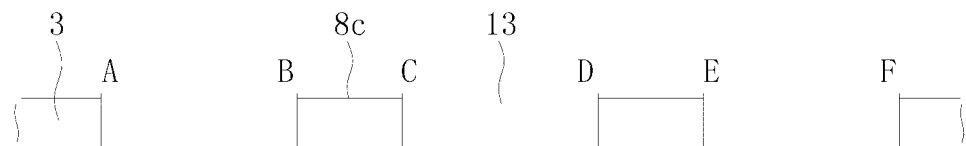
FIG. 31 is a schematic structural view of a plurality of guiding members distributed along the axial direction of the tube in the bendable sheath of the present disclosure.

Referring to FIG. 31, in order to better play the role of the guiding member 13, in one embodiment, a plurality of guiding members 13 may be provided which are spaced-apart from each other along the axial direction of the tube to form a plurality of guiding portions for delimiting the gap between the tube 3 and the movable section 8c. The plurality of guiding portions limits the extension direction of the corresponding portions of the movable section 8c, and thus delimits the gap between the movable section 8c and the tube 3.

It can be seen from the figure that three guiding members, which are arranged around the tube 3 and spaced-apart from each other, include a guiding member AB, a guiding member CD, and a guiding member EF. The spacing distances among the three guiding members may be the same or different. In other words, in the case where the tube 3 is provided with a plurality of guiding members 13, the spacing distances between two adjacent guiding members 13 may be the same or different, or partially the same, and the guiding members 13 may be arranged flexibly.

Furthermore, the lengths of the guiding members AB, CD, and EF may be the same or different or partially the same. In other words, in the case where the tube 3 is provided with a plurality of guiding members 13, the lengths of the guiding members 13 may be the same, or different, or partially the same, and the configuration of each of the guiding members 13 may be provided flexibly.

Further, in the case where the guiding member EF is configured as the guiding member that is located at the most distal position, the distal end of the movable section 8c may be located within the guiding member EF, or further extend out of the guiding member EF.

In the case where the guiding member AB is configured as the guiding member that is located at the most proximal position, the proximal end of the movable section 8c may be located within the guiding member AB, or further extend out of the guiding member AB.

In order to adapt to the variety of the gap between the tube 3 and the movable section 8c, the guiding member 13 may be configured as a radial expandable structure, which has an undeformed configuration in which the guiding member 13 constrains the movable section 8c against the outer wall of the tube, and a deformed configuration in which the guiding member 13 is locally separated from the tube under the influence of the movable section 8c.

When the movable section 8c is not pulled, the guiding member 13 can constrain the movable section on the outer wall of the tube, which, on the one hand, prevents the movable section from being exposed to cut or scratch the aorta, and on the other hand, makes the overall structure of the delivery system compact and thus facilitates the delivery of the delivery system into the aorta.

When the movable section 8c is pulled, the gap between the movable section 8c and the tube 3 will be changed, and the movable section 8c will apply a radial and outward expanding force to the guiding members 13 that constrain the movable section 8c. Due to a constraining structure formed between each guiding member 13 itself and the tube 3, which will still constrain the guiding member 13 after the movable section 8c applies force to the guiding members 13, the guiding members 13 will be locally separated from the tube under the influence of the movable section, and thus form a plurality of spaces that are spaced-apart from each other and define the gap between the movable section and the tube.

Figure 32:
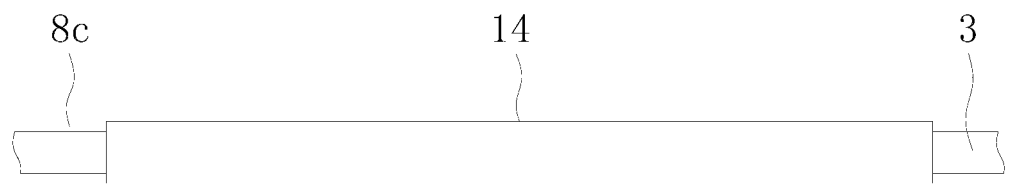
FIG. 32 is a schematic structural view of the guiding sleeve in the bendable sheath of the present disclosure.

Compared with FIG. 31, in another embodiment as shown in FIG. 32, the guiding members 13 may be continuously distributed along the axial direction of the tube to form a guiding channel for defining the gap between the tube 3 and the movable section. The formed guiding channel limits the overall extension direction of the movable section 8c.

It should be noted that the continuous guiding channel formed by the guiding member 13 may be formed by a single guiding member 13 that extends along the axial direction of the tube, or may be formed by a plurality of guiding members that are continuously distributed and connected.

In order to better guide the movable section 8c, the guiding member 13 may be configured as a guiding sleeve 14 that is connected around the outer periphery of the tube and surrounds the movable section.

It can be seen from the figure that the guiding sleeve 14 has two ends A and B. The end A may be configured as the proximal end of the guiding sleeve 14 and the end B may be configured as the distal end of the guiding sleeve 14. The distal end of the movable section 8c may be located within the guiding sleeve 14, or may further extend through the end B. The proximal end of the movable section 8c may be located within the guiding sleeve 14, or may further extend through the end A.

The guiding sleeve 14 itself may be configured as a radial expandable structure to better define the gap between the tube 3 and the movable section.

To simplify the structure of the guiding sleeve 14, in one embodiment, the guiding sleeve 14 may be made of a flexible material. A part of, or the whole of, the guiding sleeve 14 may be made of the flexible material. The flexibility of the flexible material is sufficient such that the guiding sleeve 14 can assume the undeformed configuration where the movable section is driven against the outer wall of the tube, and the deformed configuration where the guiding sleeve 14 is locally separated from the tube under the influence of the movable section.

When the guiding sleeve 14 assumes the deformed configuration, the deformed configuration can only be maintained under the sustained action of the movable section 8c. When the action from the movable section 8c to the guiding sleeve 14 changes, the degree of the local separation between the guiding sleeve 14 and the tube 3 changes accordingly. After the action from the movable section 8c is released, the guiding sleeve 14 will drive the movable section 8c against the outer wall of the tube 3 under the flexibility of the flexible material to return to the undeformed configuration.

Figure 33:
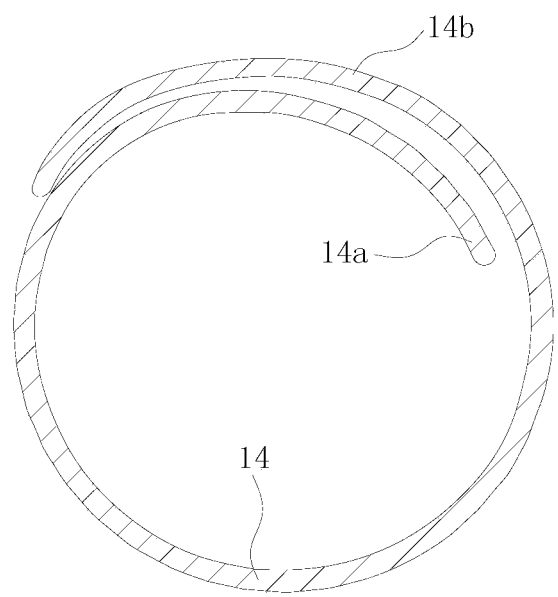
FIG. 33 is a schematic cross-sectional view of the guiding sleeve of the bendable sheath of the present disclosure with the guiding sleeve configured as a coiled structure (in an undeformed configuration)

Referring to FIG. 33, in another embodiment, the guiding sleeve 14 is configured as a coiled structure, that is, the cross section of the guiding sleeve 14 is coil-shaped. The coiled structure is configured such that the guiding sleeve 14 itself is partially overlapped in the circumferential direction, and has a deformed configuration in which the guiding sleeve 14 is locally separated from the tube and the corresponding portions of the coiled structure are unfolded, and an undeformed configuration in which the coiled structure automatically returns to drive the movable section to closely contact with the outer wall of the tube.

The guiding sleeve 14 in the undeformed configuration constrains the movable section against the outside of the tube.

In order to drive the movable section against the outer wall of the tube, the coiled structure in the undeformed configuration may be coiled circumferentially by more than one circle, and the portion extending beyond 360 degrees overlaps with the portion within 360 degrees.

In other words, on the same cross section of the guiding sleeve 14 in the undeformed configuration, the coiled structure runs circumferentially by more than 360 degrees from the starting end 14a to the terminal end 14b, wherein the portion extending beyond 360 degrees overlaps with the portion within 360 degrees. It can be seen from the figure that the terminal end 14b of the guiding sleeve 14 extends circumferentially more than one circle relative to the starting end 14a, and overlaps the circumference of the starting end 14a, so that a complete channel can be formed within the guiding sleeve 14.

Since the guiding sleeve 14 is required to automatically return to the undeformed configuration of the coiled structure without the influence of the movable section, the overlapping portions preferably have smooth contact surfaces, that is, the overlapping portions do not have configurations or members that would block each other and prevent the guiding sleeve 14 from returning to the undeformed configuration.

Figure 34:
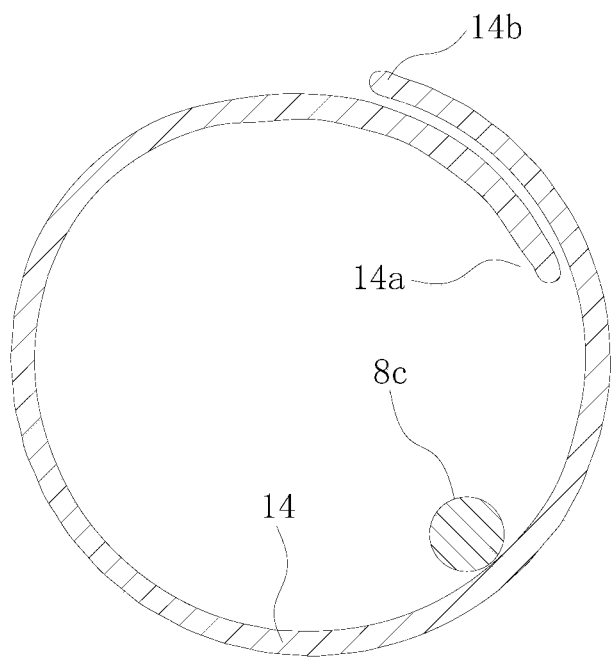
FIG. 34 is a schematic cross-sectional view of the guiding sleeve of the bendable sheath of the present disclosure with the guiding sleeve configured as a coiled structure (in a deformed configuration)

Referring to FIG. 34, when the coiled structure is subjected to a radial force from the movable section 8c, the overlapping portions of the coiled structure will be expanded accordingly, while the coiled structure always extends more than or equal to 360 degrees. In other words, in any case that the guiding sleeve 14 assumes the undeformed configuration or the deformed configuration, the coiled structure always has portions that are partially overlapped with each other to maintain the complete channel, and to prevent the movable section 8c from being exposed, thereby ensuring safety.

Figure 35:
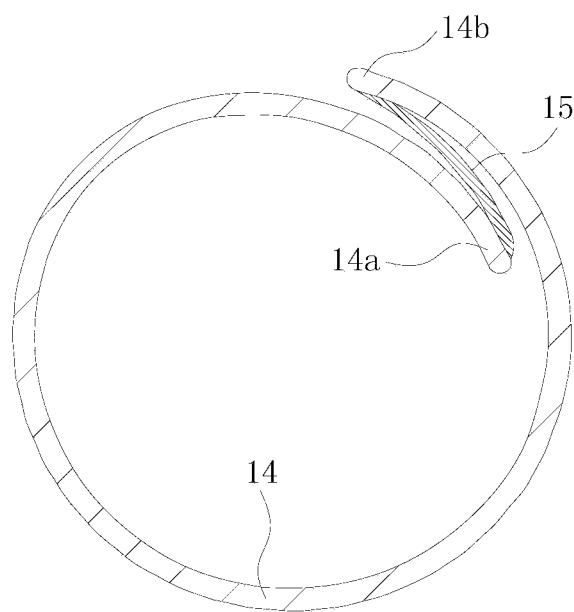
FIG. 35 is a schematic cross-sectional view of a guiding sleeve provided with a flexible film in the bendable sheath of the present disclosure.

Referring to FIG. 35, in order to allow the coiled structure to transform between the deformed configuration and the undeformed configuration more flexibly, the starting end 14a and the terminal end 14b of the coiled structure coiled in the circumferential direction may be connected by a flexible film 15 to ensure that the coiled structure can automatically return to the undeformed configuration after the external force is released, and to maintain a certain strength and compliance of the coiled structure.

The flexible film 15 mainly functions to provide a radial supporting force to prevent the coiled structure from being excessively expanded under the radial force of the movable section 8c and from failing to serve as the guiding sleeve 14. At the same time, the sealing of the guiding channel formed by the guiding sleeve 14 can be improved, and the movable section 8c can be prevented from sliding out of the guiding sleeve 14 from the gap where the starting end 14a and the terminal end 14b overlap with each other.

Since the flexible film 15 would be folded or twisted when the guiding sleeve 14 transforms between the deformed configuration and the undeformed configuration, the thickness and rigidity of the flexible film 15 may be smaller than that of the guiding sleeve 14. In this embodiment, the flexible film 15 may be made of PTFE material with a thickness of 0.25 mm to 0.5 mm.

In any case that the guiding sleeve 14 assumes the undeformed configuration or the deformed configuration, the flexible film 15 can keep the guiding sleeve 14 closed. The flexible film 15 may be fixed to the guiding sleeve 14, and for example, by welding.

In order to receive the flexible film 15, the flexible film 15 may be located between the overlapping portions of the guiding sleeve 14. The flexible film 15 may extend for a section in the circumferential direction, that is, it does not extend 360 degrees to cover the entire inner cavity of the guiding sleeve 14. When the guiding sleeve 14 assumes the undeformed configuration, the flexible film 15 may be tensioned between the starting end 14a and the terminal end 14b of the guiding sleeve 14. The fixing portions between the flexible film 15 and the guiding sleeve 14 are not strictly required to be located at the starting end 14a and the terminal end 14b, and may be adjusted appropriately.

In another embodiment, in order to provide the constraining structure between the guiding sleeve 14 and the tube 3, at least a part of the guiding sleeve 14 is fixed to the tube 3.

Since the guiding sleeve 14 needs to be locally separated from the tube 3 following the movable section 8c when defining the gap between the tube 3 and the movable section 8c, the distal and proximal ends of the guiding sleeve 14 may be fixed on the outer periphery of the tube 3, and the section of the guiding sleeve 14 between the distal end and the proximal end may be movably arranged on the outer periphery of the tube 3, so as to adapt to the possible varying of the gap between the portion of the guiding sleeve 14 and the tube.

The guiding sleeve 14 may be connected and fixed to the tube 3 by welding or bonding, and the section of the guiding sleeve 14 between the distal end and the proximal end may be movably arranged on the outer periphery of the tube 3. The movable arrangement can be understood as there is no additional constraint or connection between the guiding sleeve 14 and the tube 3, and the guiding sleeve 14 holds in the positions relative to the tube 3, only depending on its own strength or flexibility. For example, the guiding sleeve 14 may be made of a flexible material and thus is capable of being constrained around the outer periphery of the tube 13.

Both the distal end and the proximal end of the movable section 8*c* closely contact the tube 3 under the constraint of the tube 3 or an external force. Therefore, after the movable section 8*c* is pulled, the movable section 8*c* is tensioned, and the corresponding portion of the tube 3 assumes a bent configuration. The guiding sleeve 14 may generally delimit the gap between the tube 3 and the movable section at any position in the axial direction. Therefore, in one embodiment, at least a part of the movable section 8*c* may be located within the radial gap between the tube 3 and the guiding sleeve 14. The movable section 8*c* will be locally guided by the guiding sleeve 14, and the gap between the movable section 8*c* and the tube 3 will be generally delimited by the local limiting of the guiding sleeve 14 to the movable section 8*c*, so as to achieve the expected limiting effect.

In order to obtain the optimal limiting effect and the optimal safety performance, in another embodiment, the whole movable section 8*c* may be located within the radial gap between the tube 3 and the guiding sleeve 14. At this time, the distal end and the proximal end of the movable section 8*c* may be located at the ends of the guiding sleeve 14, respectively, or be located between the proximal end and the distal end of the guiding sleeve 14.

The movable section 8*c* may be partially or entirely located within the radial gap between the tube 3 and the guiding sleeve 14 using various techniques to extend in the radial gap. For example, in one embodiment, the movable section 8*c* may be movably arranged within the radial gap between the tube 3 and the guiding sleeve 14. The movable arrangement can be understood as there being no additional constraint or connection between the movable section 8*c* and the guiding sleeve 14 and the tube 3, and the movable section 8*c* is located within the radial gap between the tube 3 and the guiding sleeve 14, only depending on its own configuration. When the movable section 8*c* assumes a released configuration, it is flexibly located within the radial gap between the tube 3 and the guiding sleeve 14, and when the movable section 8*c* is pulled to assume a tensioned configuration, a force will be applied to the guiding sleeve 14 from the movable section 8*c*.

In another embodiment, the movable section 8*c* may be locally and slidably attached on the inner side of the guiding sleeve 14. The movable section 8*c* may be locally constrained by the inner side of the guiding sleeve in the radial direction, but can move relative to the inner side of the guiding sleeve in the axial direction. The movable section 8*c* may be partially constrained by the inner side of the guiding sleeve in the radial direction, which can prevent the movable section 8*c* from extending in a disorder manner, or even becoming knotted when the movable section 8*c* is not pulled and tensioned. The movable section 8*c* can move relative to the inner side of the guiding sleeve in the axial direction, which ensures that the constraint of the guiding sleeve 14 would not be affected when the movable section 8*c* is pulled.

Figure 36:
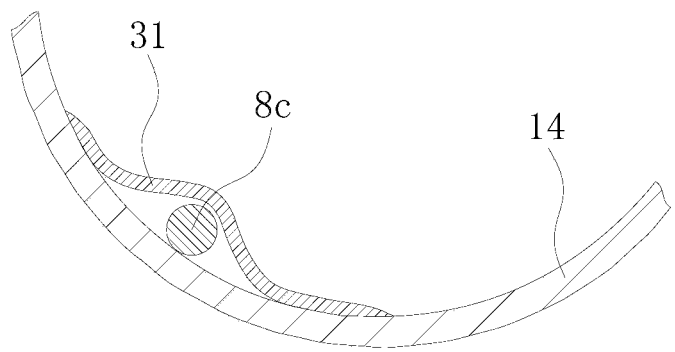
FIG. 36 is a schematic structural diagram of the movable section in the bendable sheath of the present disclosure constrained to the inner side of the guiding sleeve by the limiting ring.

Referring to FIG. 36, the movable section 8*c* is locally and slidably attached on the inner side of the guiding sleeve 14 using the following technique: the guiding sleeve 14 may be provided with a double-layered structure 31, and a part of the movable section 8*c* may extend within the double-layered structure 31 to allow the movable section 8*c* to slidably attach on the inner side of the guiding sleeve 14.

The inner layer of the double-layered structure 31 may include a plurality of sections that are spaced-apart from each other. The movable section 8*c* may pass through the double-layered structure 31 at the plurality of sections in sequence and thus be constrained at a plurality of positions. The inner layer of the double-layered structure 31 may also be configured as a continuous section, which continuously constrains the movable section 8*c*.

The outer layer of the double-layered structure 31 may be regarded as the entire guiding sleeve, and the inner layer may be configured as the layer that is unclosed in the circumferential direction, as shown in the figure. Alternatively, the inner layer may be tubular, and the movable section 8*c* may extend within the inner layer.

The movable section 8*c* extends within the double-layered structure 31 and may be constrained by the inner side of the guiding sleeve 14. The constrained portion relative to a specific portion of the movable section 8*c* is not fixed, but changes with the movement of the movable section 8*c*.

The movable section 8*c* is locally and slidably engaged on the inner side of the guiding sleeve 14 using another technique: the movable section 8*c* may be locally and slidably attached on the inner side of the guiding sleeve 14 by means of stitching.

In this technique, the movable section 8*c* itself may function as a suture, and the movable section 8*c* itself may be stitched on the guiding sleeve 14 to allow the movable section 8*c* to locally and slidably attach on the inner side of the guiding sleeve 14.

Figure 37:
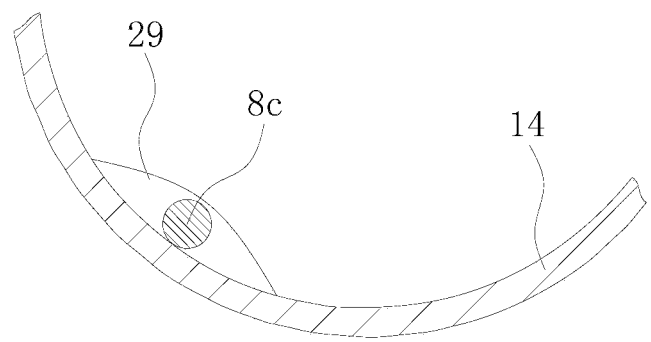
FIG. 37 is a schematic structural diagram of the movable section of the bendable sheath of the present disclosure stitched on the inner side of the guiding sleeve.

Referring to FIG. 37, other sutures 29 may also be used to stitch the movable section 8*c* on the guiding sleeve 14 so as to allow the movable section 8*c* to locally and slidably attach on the inner side of the guiding sleeve 14.

In the case where the movable section 8*c* is locally and slidably attached on the inner side of the guiding sleeve 14 by stitching, the local portion of the movable section 8*c* that is attached on the inner side of the guiding sleeve 14 is changeable. In other words, when the movable section 8*c* assumes the tensioned configuration or the released configuration, the aforementioned local portion is changeable relative to a specific portion of the movable section 8*c*.

The guiding sleeve 14 surrounds the movable section to prevent the movable section 8*c* from cutting or scratching the aorta. When the guiding sleeve 14 surrounds the movable section, the guiding sleeve 14 and the tube 3 may be arranged side by side, and the movable section 8*c* extends within the guiding sleeve 14. The guiding sleeve 14 may be fixed on the outer wall of the tube 3 by continuously or discontinuously fixing the attachment portion of the guiding sleeve 14.

When the movable section 8*c* is pulled and tensioned under a force, a radial force will be applied to the guiding sleeve 14 from the movable section 8*c*. Then the guiding sleeve 14 will be locally moved with the movement of the movable section to delimit the gap between the tube 3 and the movable section 8*c*.

When the guiding sleeve 14 surrounds the movable section, the tube 3 and the guiding sleeve 14 may overlap with each other in the circumferential direction, that is, the guiding sleeve 14 may surround a part of the tube 3 in the circumferential direction. The movable section 8c may be located within the space where the guiding sleeve 14 overlaps with the tube 3, and be limited by the portion of the guiding sleeve 14 surrounding the tube 3.

In the case where the guiding sleeve 14 has no flexibility, the guiding sleeve 14 can be attached to the outer wall of the tube 3 as much as possible by pulling the pull wire 8. The resulting delivery system has a compact structure and is convenient for storage. It should be noted that the purpose of appropriately pulling the pull wire 8 is not to bend the sheath, but to gather the guiding sleeve 14.

Figure 38:
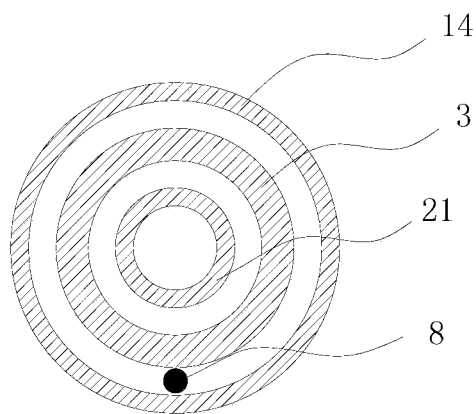
FIG. 38 is a schematic cross-sectional view of the guiding sleeve of the bendable sheath of the present disclosure with the guiding sleeve configured as a cylindrical structure.

Referring to FIG. 38, in another embodiment, in order to optimize the flexibility of the guiding sleeve 14, and at the same time, to facilitate the adjustment of the action point on the tube 3 during bending the pull wire 8, the guiding sleeve 14 may be cylindrical and surround the tube 3 by one circle in the circumferential direction.

Both ends of the guiding sleeve 14 may be movably surrounded around the outside of the tube, or at least one end of the guiding sleeve 14 may be fixed, and for example, by bonding, and thus be limited by the tube 3. A gap will be formed between the middle of the guiding sleeve 14 and the tube 3 when the movable section is tensioned, so an additional constraining structure is not necessary.

In the case where the guiding sleeve 14 is cylindrical, the movable section 8c in the released configuration may be located at any position within the radial gap between the guiding sleeve 14 and the tube 3. When the movable section 8c is tensioned, the movable section 8c will move from the original position and run along the path defined by the distal and proximal ends of the movable section 8c, to drive the tube 3 to bend at a predetermined angle.

Figure 39A:
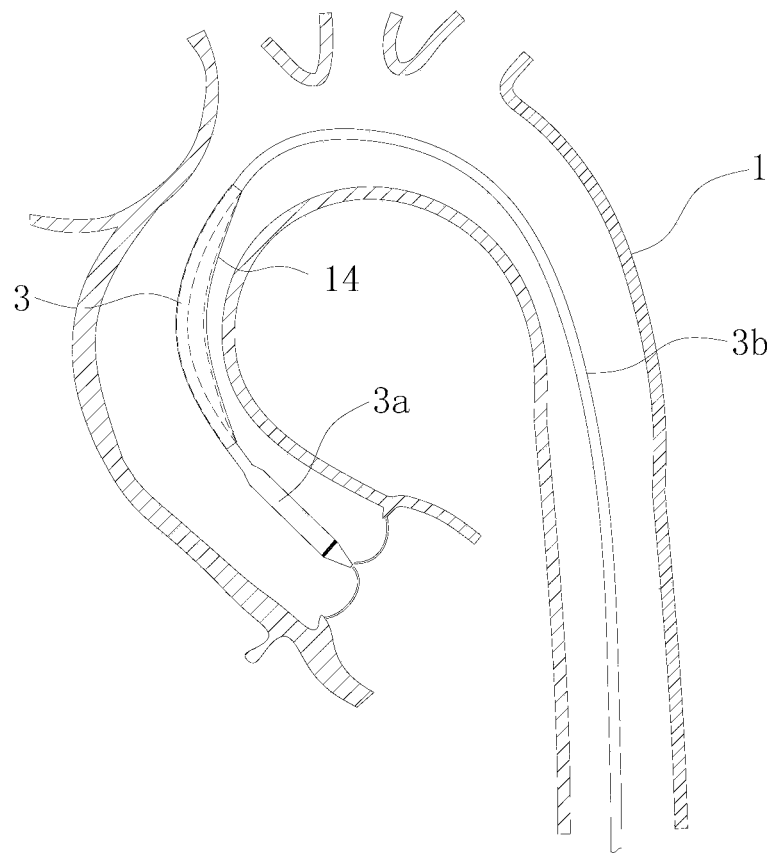
FIG. 39a is a schematic diagram of the connection between the distal end of the guiding sleeve and the tube in the bendable sheath of the present disclosure.

Referring to FIG. 39a, the tube 3 may include an expandable section 3a at the distal end for accommodating an implantable instrument, and a connection section 3b connected to the expandable section 3a and extending towards the proximal end. The guiding sleeve 14 may be connected to the outer periphery of the tube 3. Specifically, the entire the guiding sleeve 14 may be connected to the connection section 3b of the tube 3. The distal end of the guiding sleeve 14 may be fixed at a position of the connection section 3b adjacent to the expandable section 3a, which allows the guiding sleeve 14 to surround the movable section 8c to a greater extent, and at the same time, avoids affecting the expandable section 3a to release the implantable instrument.

The proximal end of the guiding sleeve 14 may extend towards the proximal end of the tube 3, so that the guiding sleeve 14 may surround a part or the whole of the movable section 8c.

Figure 39B:
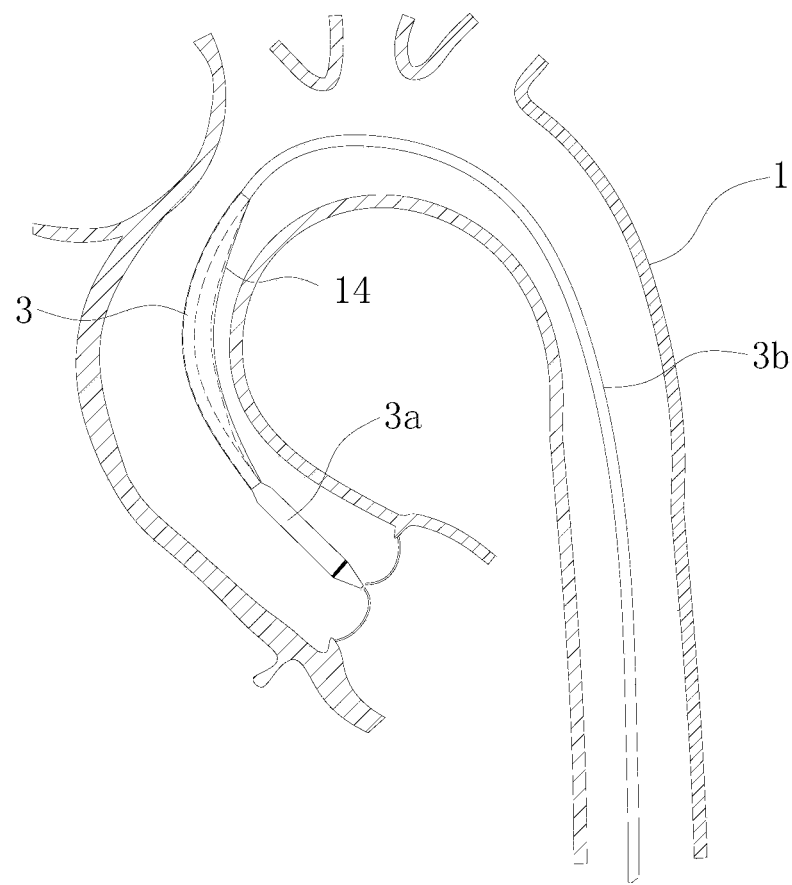
FIG. 39b is another schematic diagram of the connection between the distal end of the guiding sleeve and the tube in the bendable sheath of the present disclosure.

Compared with FIG. 39a, in another embodiment as shown in FIG. 39b, the distal end of the guiding sleeve 14 may be fixed at the junction of the connection section 3b and the expandable section 3a, so as to reduce the number of the visible connection portions on the outer wall of the tube and thus improve the appearance.

The proximal end of the guiding sleeve 14 may be connected to the connection section 3b of the tube 3, and may extend towards the proximal end of the tube 3 to surround a part or the whole of the movable section 8c.

Figure 39C:
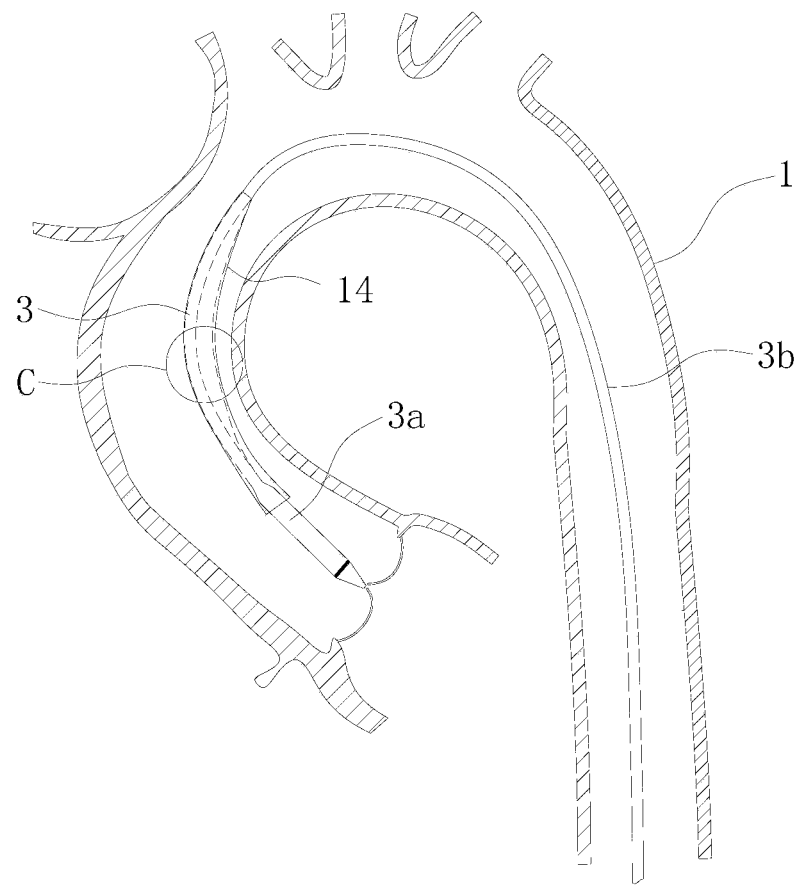
FIG. 39c is another schematic diagram of the connection between the distal end of the guiding sleeve and the tube in the bendable sheath of the present disclosure.

Compared with FIG. 39a, in another embodiment as shown in FIG. 39c, in order to allow the guiding sleeve 14 to surround the movable section 8c to a greater extent, the distal end of the guiding sleeve 14 may be fixed on the expandable section 3a and be close to the proximal end of the expandable section 3a. The proximal end of the guiding sleeve 14 may be connected to the connection section 3b of the tube 3 and extend towards the proximal end of the tube 3.

As shown in FIGS. 39a to 39c, the tube 3 assumes a bent configuration. At this time, the movable section 8c closely contacts with the inner wall of the guiding sleeve 14. The guiding sleeve 14 will be locally separated from the tube 3 under the radial force of the movable section 8c and form a space limiting the tube 3 and the movable section 8c.

Figure 39D:
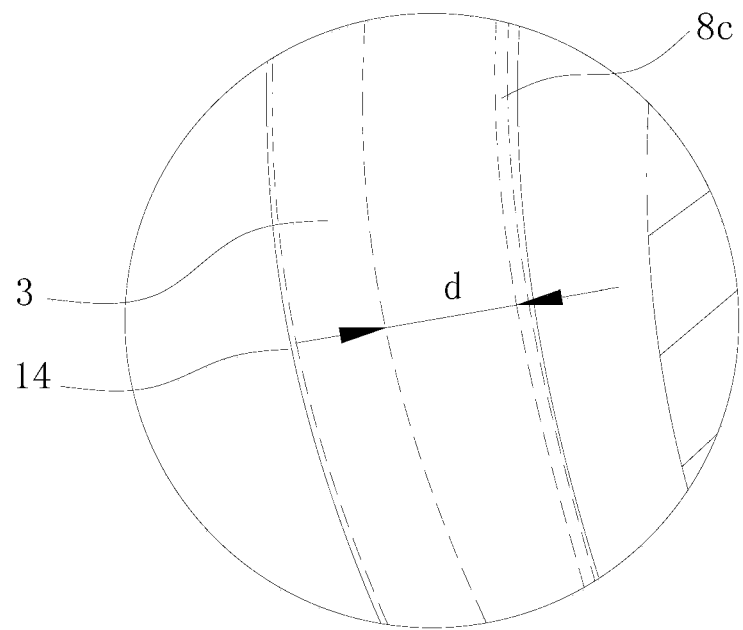
FIG. 39d is an enlarged view of part C of FIG. 34c.

Referring to FIG. 39d, the guiding sleeve 14 surrounds the tube 3 and the movable section 8c. When the movable section 8c is pulled and tensioned, the movable section 8c may be locally or entirely attached to the inner side of the guiding sleeve 14 and a gap with a distanced will be formed between the movable section 8c and the tube 3. The distance d of the gap is limited by the guiding sleeve 14 to improve the bending sensitivity.

Since the movable section 8c exerts a large force on the guiding sleeve 14 when the former is pulled and tensioned, and the movable section 8c has a thin configuration, the contact area between the movable section 8c and the guiding sleeve 14 will be small, and the pressure applied from the movable section 8c to the guiding sleeve 14 will be large. Therefore, it is necessary to partially or entirely reinforce the guiding sleeve 14. At least the side wall of the guiding sleeve should be provided with a reinforced area that contacts and engages with the movable section.

The specific structure of the reinforced area is not limited on the premise that the strength of the reinforced area is sufficient. For example, the reinforced area may have a larger thickness than the "other neighboring area".

The "other neighboring area" refers to the other area of the guiding sleeve 14 adjacent the reinforced area, i.e., the other area of the guiding sleeve 14 except for the reinforced area. The supporting strength to the movable section 8c may be enhanced using the technique of increasing the thickness of the reinforced area which is a relatively simple technique.

The thickness may be increased using one of the following techniques: the reinforced area may be designed with a larger thickness in which case the guiding sleeve 14 is formed in one piece with the reinforced area being a part of the one piece; or a reinforcing material may be added to a formed guiding sleeve 14 to form the reinforced area in which case the reinforced area may be configured as a multi-layer structure and partially connected with the formed guiding sleeve.

The reinforcing material may be connected to the guiding sleeve 14, and for example, by welding or bonding, and the reinforcing material may be connected to the inner or outer wall of the guiding sleeve, and the reinforcing material may cover a part or the whole of the guiding sleeve 14.

In another embodiment, a reinforcement layer may be provided in the side wall of the reinforced area to obtain sufficient strength. The reinforcement layer is provided such that it would not produce an adverse effect on the limiting of the guiding sleeve 14.

Different from the technique of adding the reinforced area on the inner or outer wall of the guiding sleeve 14, the reinforcement layer is arranged in the side wall of the guiding sleeve 14 in this embodiment and is formed as one piece together with the inner or outer wall of the guiding sleeve 14. That is, the reinforcement layer is built in the guiding sleeve 14, which is not easy to be affected by external factors, and can better cooperate with the guiding sleeve 14.

Figure 40A:
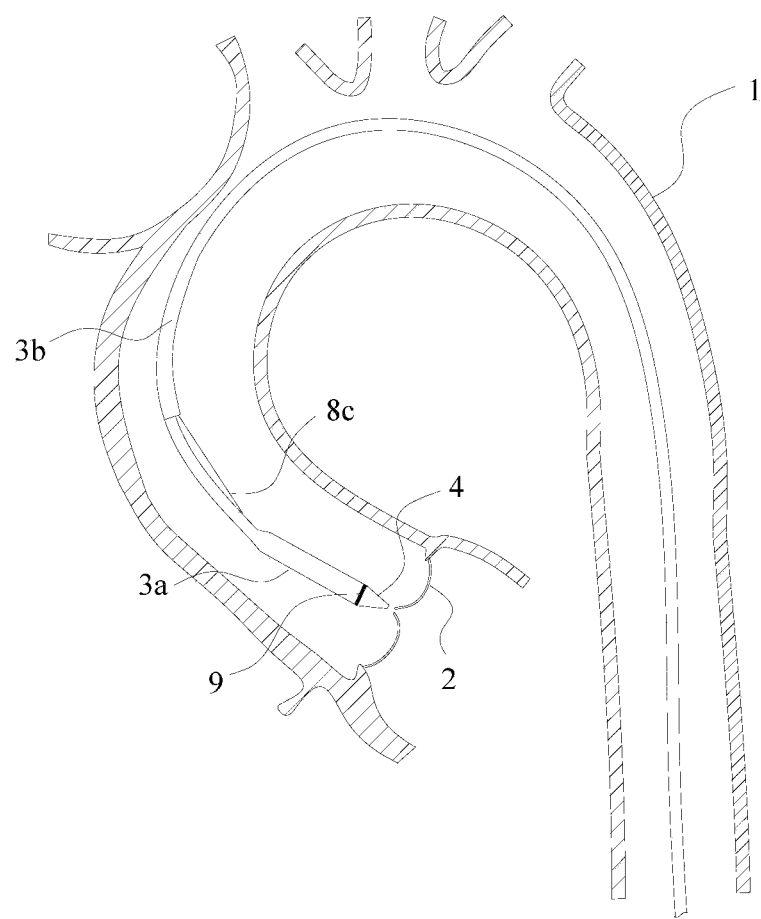
FIG. 40a is a schematic diagram of the connection position between the distal end of the movable section and the tube in the bendable sheath of the present disclosure.

Referring to FIG. 40a, the tube 3 may include an expandable section 3a at the distal end for accommodating an implantable instrument, and a connection section 3b connected to the expandable section 3a and extending towards the proximal end.

In order to clearly show the movable section 8c in the figure and avoid interference, the guiding sleeve is not shown in the corresponding figures of this embodiment. The guiding sleeve may be provided as required, and the configuration and connection of the guiding sleeve can be referred to using the foregoing embodiments.

The movable section 8c is the section of the pull wire 8 that is movable outside the tube. A radial gap is formed between the movable section 8c and the tube 3, which will guide the tube 3 to bend when the movable section 8c is pulled and tensioned, so the axial position of the movable section 8c on the tube 3 has an important influence on the bending of the tube 3.

It can be seen from the figure that the entire movable section 8c is located on the connection section 3b, and the distal end of the movable section 8c is fixed at a position of the connection section 3b adjacent to the expandable section 3a, which lowers the influence on the expandable section 3a provided that a good bending effect is ensured. The other section of the pull wire 8 except for the movable section 8c may extend inside the tube 3, or may be attached to the outer wall of the tube 3 by a constraining structure, such as a flexible sleeve, which surrounds the tube 3.

Figure 40B:
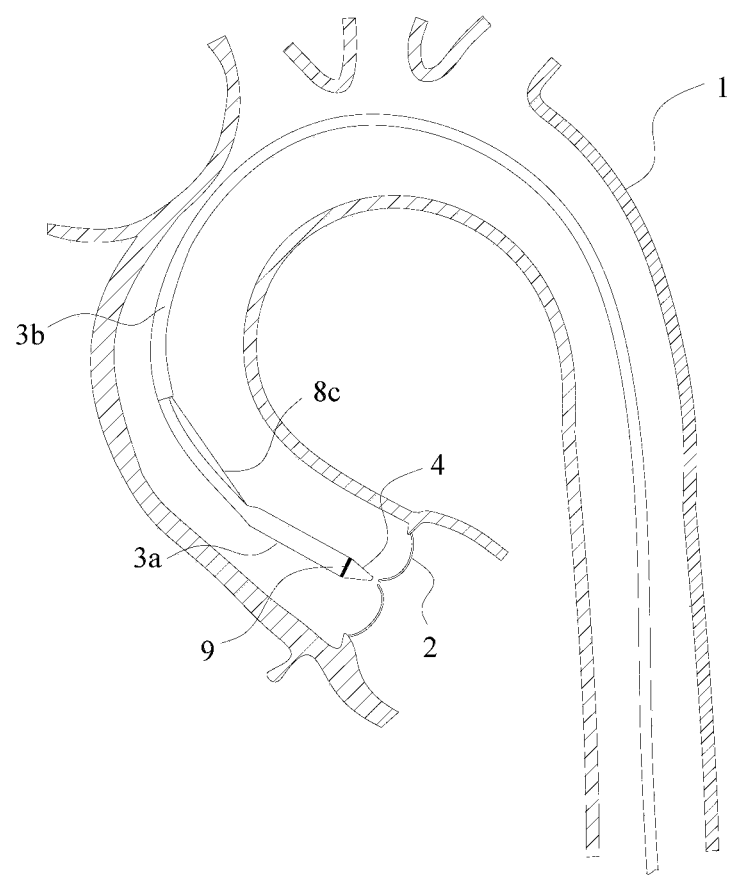
FIG. 40b is another schematic diagram of the connection position between the distal end of the movable section and the tube in the bendable sheath of the present disclosure.

Compared with FIG. 40a, in another embodiment as shown in FIG. 40b, the distal end of the movable section 8c may be fixed at the junction of the connection section 3b and the expandable section 3a. The connection structure at the junction can reduce the difficulty of fixing the movable section 8c to a certain extent.

Figure 40C:
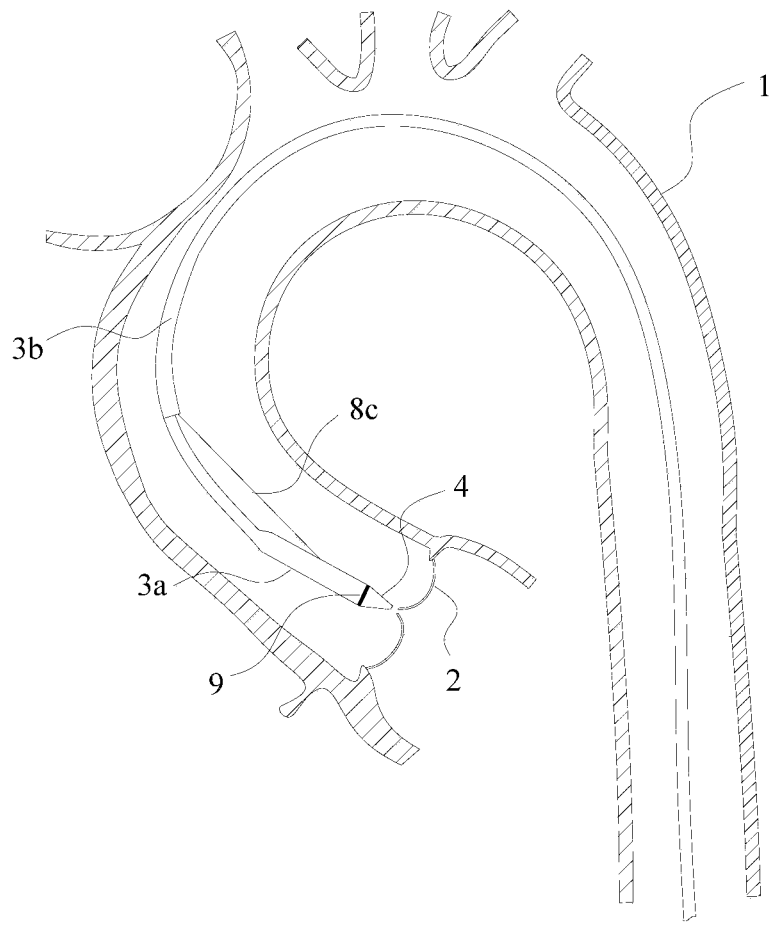
FIG. 40c is another schematic diagram of the connection position between the distal end of the movable section and the tube in the bendable sheath of the present disclosure.

Compared with FIG. 40a, in another embodiment as shown in FIG. 40c, the distal end of the movable section 8c may be fixed on the expandable section 3a. When the movable section 8c is fixed on the expandable section 3a, the distal end of the movable section 8c will be closer to the distal end of the tube 3, which improves the bending sensitivity of the tube 3.

In the case where the distal end of the movable section 8c is fixed on the expandable section 3a, the distal end of the movable section 8c may be fixed on the expandable section 3a and close to the proximal end of the expandable section 3a, or be fixed on the expandable section 3a and close to the distal end of the expandable section 3a, or be fixed on the expandable section 3a and between the proximal end and the distal end of the expandable section 3a.

Figure 41:
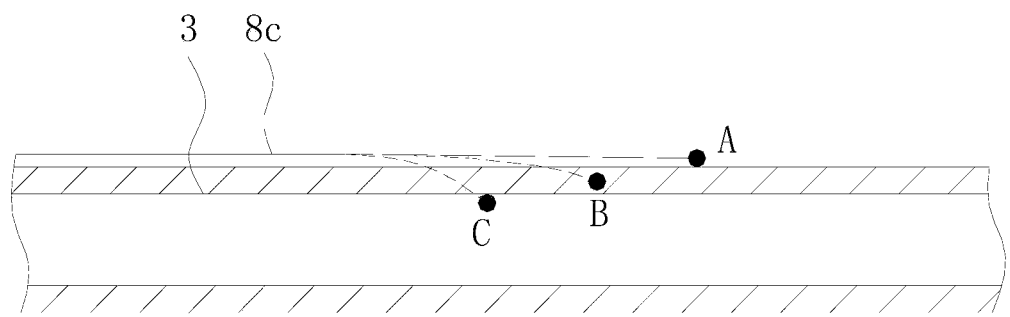
FIG. 41 is a schematic structural diagram of the distal end of the movable section fixed with the tube in the bendable sheath of the present disclosure.

Referring to FIG. 41, the movable section 8c is the section of the pull wire 8 that is movable outside the tube, the total length of the movable section will be changed after the movable section is pulled to drive the tube 3 to bend. In order to achieve the above-mentioned bending effect, the proximal end of the movable section 8c may be changeable relative to the tube 3, and the distal end of the movable section 8c may be a fixed point relative to the tube 3.

In other words, the distal end of the movable section 8c may be fixedly connected to the tube 3, and the distal end of the movable section 8c may be fixedly connected to at least one of a point A on the outer side, a point B in the wall, and a point C on the inner side of the tube 3.

Figure 42:
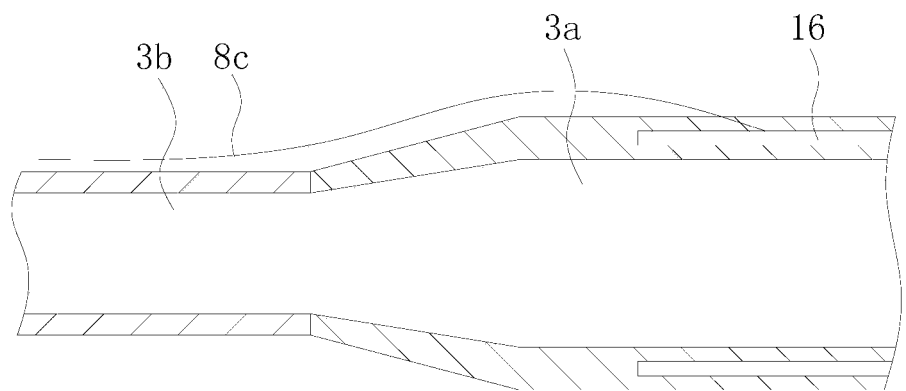
FIG. 42 is another schematic structural diagram of the distal end of the movable section fixed with the tube in the bendable sheath of the present disclosure.

Referring to FIG. 42, in another embodiment, the tube 3 may include an expandable section 3a at the distal end for accommodating an implantable instrument, and a connection section 3b connected to the expandable section 3a and extending towards the proximal end.

In the case where the distal end of the movable section 8c is fixed in the wall of the tube 3, it can be fixed in this embodiment using the following technique: the expandable section 3a of the tube 3 may be provided with an intermediate layer, and a metal reinforcing structure 16 may be provided in the intermediate layer of the expandable section 3a. The distal end of the movable section 8c may enter into the intermediate layer of the expandable section 3a and may be fixedly connected with the metal reinforcing structure 16.

Based on the technique of fixing the movable section 8c to the metal reinforcing structure 16, the requirement for the structural strength of the tube can be reduced, and at the same time, since the action area from the metal reinforcing structure 16 to the tube 3 is larger than that the action area from the distal end of the movable section to the tube 3, the bending process will be more labor-saving and convenient, with a good bending effect.

In the fixing methods of this embodiment, not only the metal reinforcing structure 16 can be provided in the intermediate layer of the expandable section 8c, that is, the movable section 8c may be not limited to be fixed on the metal reinforcing structure 16, and may be connected to any reinforcing structure provided in the intermediate layer of the expandable section 3a. Alternatively, the movable section 8c itself can be connected in the intermediate layer of the expandable section 8c by welding or bonding.

The movable section 8c can guide the distal end of the tube to bend after being pulled. It can be conceivable that the proximal end of the movable section 8c must be movable, and the distal end of the movable section 8c is preferably fixed with the tube 3, so as to determine the stress point of the bent tube, thereby obtaining the ideal bending angle.

The distal end of the movable section 8c may be fixed with the tube 3 by various means, and for example, by knotting, welding or bonding. The use of welding and bonding enables the distal end of the movable section 8c to be engaged with the tube 3 at a large area, which can improve the connection strength. In comparison, knotting is more flexible and freer in operation.

Figure 43:
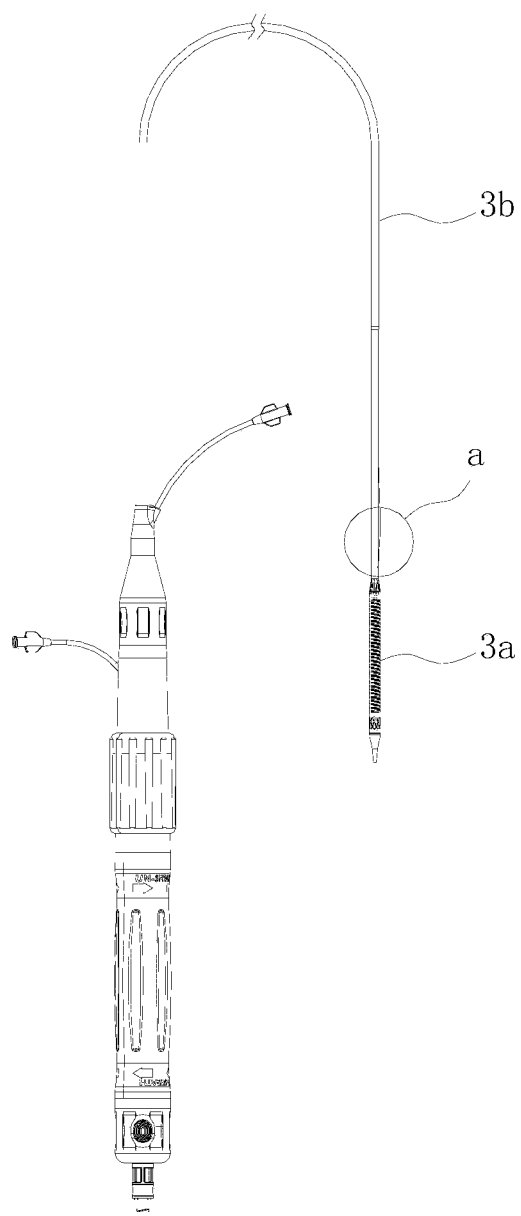
FIG. 43 is a schematic structural diagram of the bendable delivery system for an implantable valve of the present disclosure.
Figure 43A:
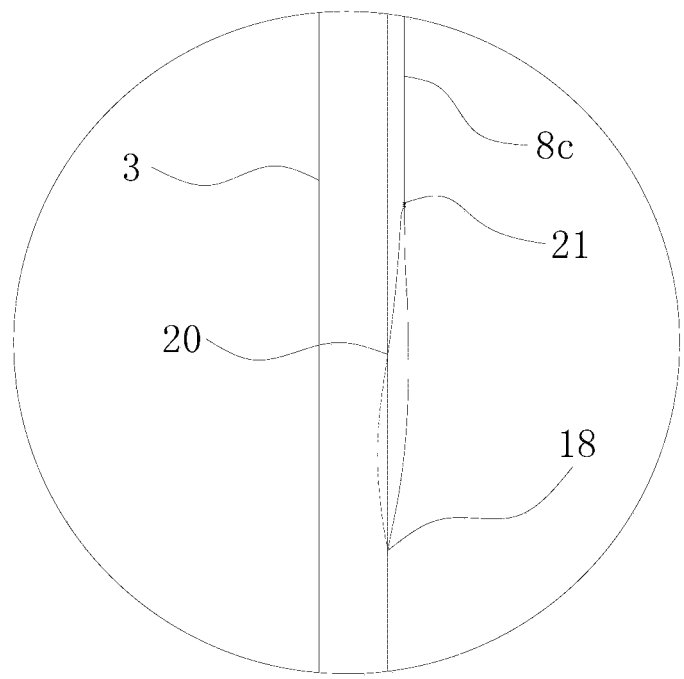
FIG. 43a is an enlarged view of part a of FIG. 43.

Referring to FIGS. 43 and 43a, in one embodiment, in the case where the distal end of the movable section 8c is connected to the tube 3 by knotting, the distal end of the movable section 8c may enter the inner cavity of the tube from the outer wall of the tube through the first through hole 18, and then pass out of the tube 3 from the inner cavity through the second through hole 20, and is thereafter knotted with the portion of the movable section 8c outside the tube to form a knot 21.

Among them, the through hole refers to the position where the movable section 8c passes through the wall of the tube.

Compared with the technique of knotting the distal end of the movable section 8c itself only after entering the inner cavity of the tube through the first through hole 18, the knotting technique in this embodiment is more reliable as the movable section 8c substantially surrounds a part of the tube therein to prevent the knotted portion from falling off the tube 3 when the pulling force on the movable section 8c is too large.

Furthermore, the movable section 8c surrounds a part of the tube 3, and thus there will be more than one action point between the movable section 8c and the tube when the movable section 8c is pulled and tensioned, which can avoid local stress concentration on the pull wire.

Furthermore, it can be seen from the figure that, in the technique of knotting the distal end of the movable section in this embodiment, the first through hole 18 is closer to the distal end of the tube than the second through hole 20.

Figure 43B:
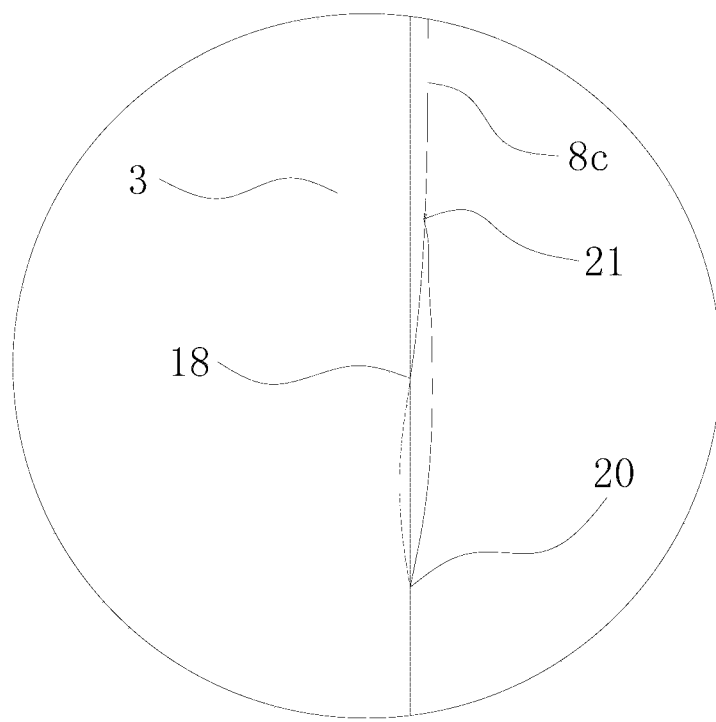
FIG. 43b is another schematic diagram of the distal end of the movable section and the tube which are connected by knotting.

Compared with FIG. 43*a*, in another embodiment as shown in FIG. 43*b*, the first through hole 18 is closer to the proximal end of the tube than the second through hole 20. In other words, the distal end of the movable section 8*c* first passes through the tube 3 through the first through hole 18, and then moves towards the distal end of the tube 3 for a certain distance in the inner cavity of the tube 3, and next passes out of the tube 3 through the second through hole 20, and subsequently moves towards the proximal end of the tube 3 for a certain distance, and thereafter is knotted with the portion of the movable section 8*c* outside the tube 3 to form a knot 21.

Figure 43C:
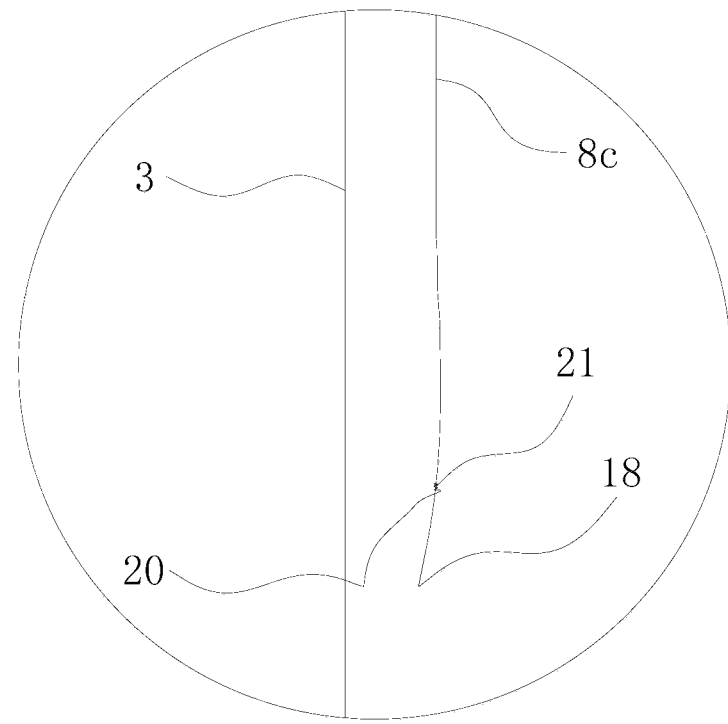
FIG. 43c is another schematic diagram of the distal end of the movable section and the tube which are connected by knotting.

Compared with FIG. 43*a*, in another embodiment as shown in FIG. 43*c*, the axial position of the first through hole 18 on the tube 3 is the same with that of the second through hole 20 on the tube 3. In other words, the distal end of the movable section 8*c* first enters the inner cavity of the tube 3 through the first through hole 18, and then moves in the circumferential direction of the tube 3 for a certain distance, and next passes out of the tube 3 through the second through hole, and subsequently moves backward in the axial direction of the tube 3, and thereafter is knotted with the portion of the movable section 8*c* outside the tube 3 to form a knot 21.

Compared with the arrangement that the first through hole 18 and the second through hole 20 are spaced-apart from each other in the axial direction of the tube 3, in this embodiment, the portion of the movable section 8*c* that is located between the first through hole 18 and the second through hole 20 can bear the pulling force applied to the tensioned movable section 8*c* to prevent the movable section 8*c* from breaking off due to an excessive pulling force.

In the case where the distal end of the movable section 8*c* is connected to the tube 3 by welding, the distal end of the movable section 8*c* may be welded to the inner wall or the outer wall of the tube 3. It is easy to understand that the welding point formed between the distal end of the movable section 8*c* and the inner wall of the tube 3 will be free of the influence of the external environment, so as to improve the reliability of the connection between the movable section 8*c* and the tube 3.

Figure 44:
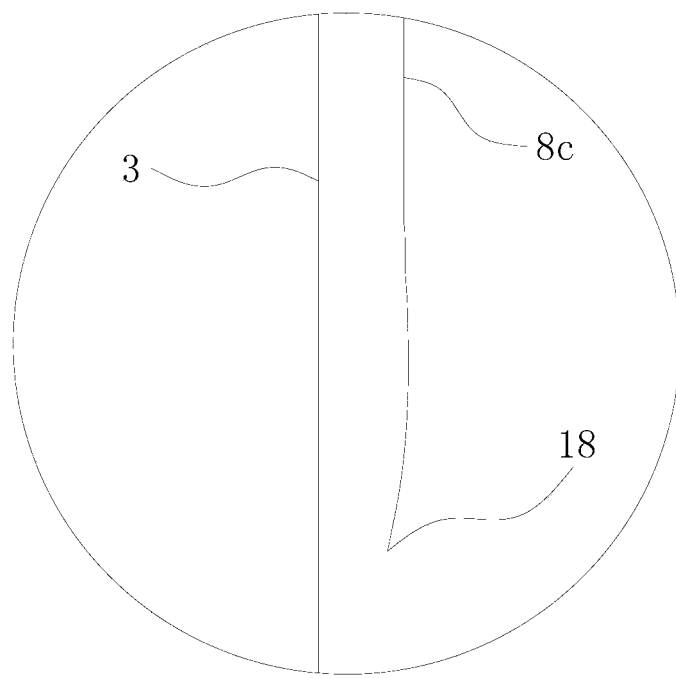
FIG. 44 is a schematic structural diagram of the distal end of the movable section and the tube which are connected by welding.

Referring to FIG. 44, the distal end of the movable section 8*c* enters the interior of the tube 3 through the first through hole 18, and is then welded and fixed at the first through hole 18.

Figure 45:
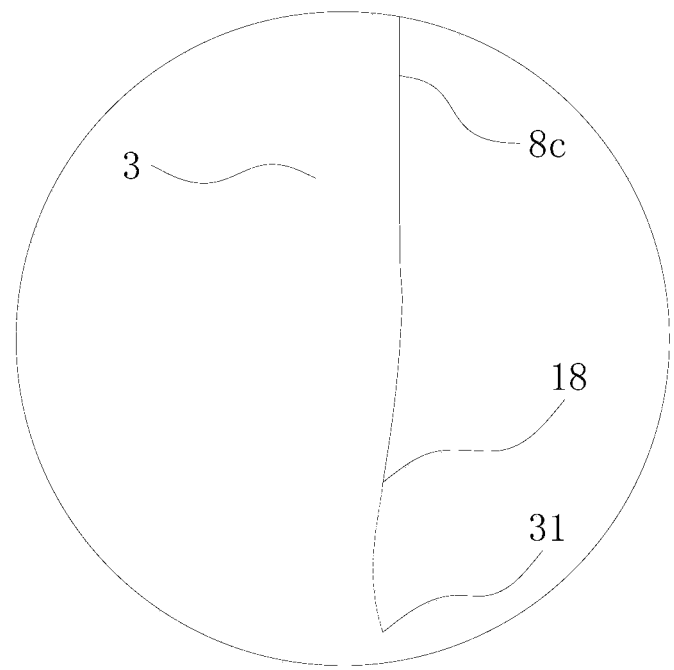
FIG. 45 is another schematic structural diagram of the distal end of the movable section and the tube which are connected by welding.

Compared with FIG. 44, in another embodiment as shown in FIG. 45, the distal end of the movable section 8*c* first enters the interior of the tube 3 through the first through hole 18, and then extends a certain distance inside the tube 3, and thereafter is welded at the welding point 31. Relative to the embodiment as shown in FIG. 44, the distal end of the movable section 8*c* in this embodiment is welded after extending a certain distance, which can reduce the influence of the through hole on the welding point.

The movable section 8*c* is the section of the pull wire 8 that is movable outside the tube, and by means of which, the bending can be performed. In order to achieve various bending effects, there may be provided one single or multiple movable sections 8*c*.

In the case where one single movable section 8*c* is provided, the movable section 8*c* can drive one portion of the tube 3 to bend, thereby controlling the guiding path of the guiding head 4 of the delivery system.

In the case where multiple movable sections 8*c* are provided which are spaced-apart from each other, after the pull wire is pulled, the multiple movable sections drive multiple portions of the tube to bend until the final bending profile arises. In comparison, in the case where multiple movable sections 8*c* are provided, the tube can be bent to a greater extent. However, the uncertainty of whether the expected effect can be achieved in this case will increase, so the number of the movable sections of the movable section should be determined as required.

It should be noted that, unless otherwise specified, in the case where multiple movable sections 8*c* are provided, the proximal end of the most proximal section may be understood as the proximal end of the entire movable sections, and the distal end of the most distal section may be understood as the distal end of the entire movable sections.

In the case where multiple movable sections 8*c* are provided, a section of the pull wire 8 between two adjacent movable sections is formed as a transition section, and the transition section may extend inside the tube, or at least closely contact with the outer wall of the tube by an external force.

Figure 46:
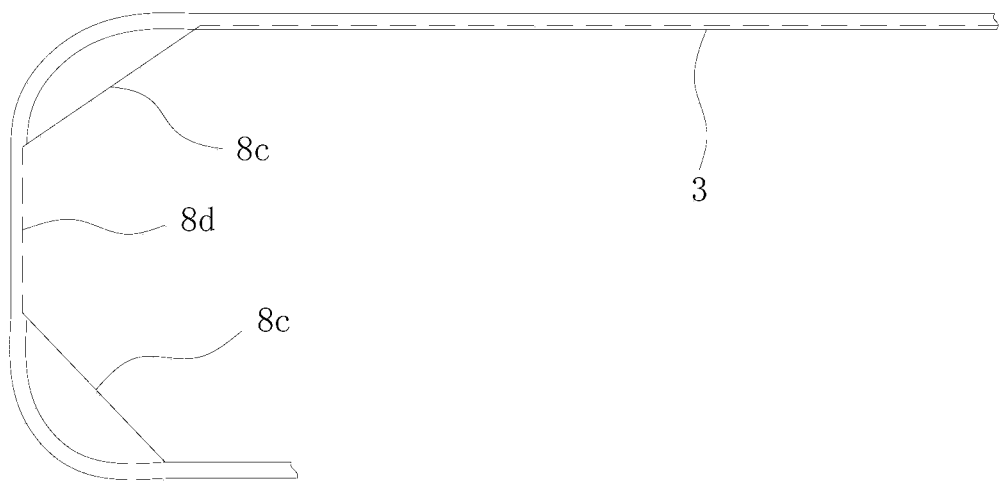
FIG. 46 is a schematic diagram of multiple movable sections.

Referring to FIG. 46, two movable sections 8*c* are taken as an example in this embodiment for further description. Each movable section 8*c* corresponds to a part of the tube 3, and the section between the two movable sections 8*c* is the transition section 8*d* that extends inside the tube.

It can be seen from the figure that when the movable section 8*c* is pulled and tensioned, the corresponding parts of the tube 3 corresponding to the movable sections 8*c* will be bent, that is, the entire bent tube 3 will have two bent portions, so that the distal end of the tube will be bent by almost 180 degrees. It should be easy to understand that the greater the number of the movable sections 8*c*, the greater the number of the bent portions of the tube 3 during bending, and thus the greater the bending angle of the entire tube 3.

Compared with the case where only one movable section is provided, in the case where multiple movable sections are provided, the tube can be driven to bend to a greater extent, and the operation required for bending to the same extent is easier.

When the movable section 8*c* is pulled and tensioned, the transition section will exert a force on the tube or a component applying an external force, to try to remove the constraint. If the transition section removes the constraint, the bending effect of the movable section will be seriously affected. Therefore, a reinforcing frame may be provided on the tube 3 at at least the transition section, or may be provided on the component that applies the external force to the transition section, to ensure the bending effect of the movable section.

Figure 47:
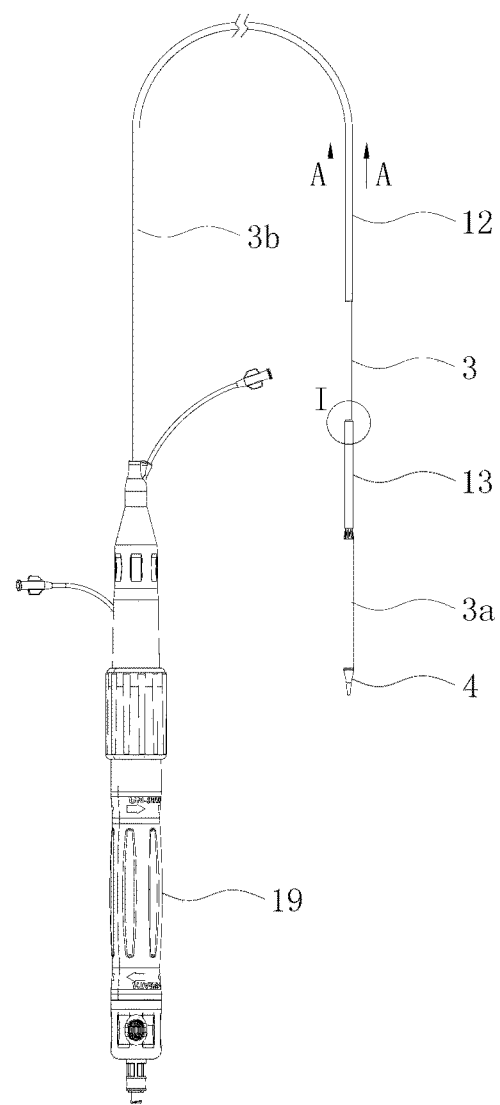
FIG. 47 is a schematic structural view of the bendable delivery system for an implantable valve of the present disclosure with a guiding sleeve added.

Referring to FIG. 47, a sleeve 12 may be provided outside the proximal end of the tube 3, and the sleeve 12 is axially and slidably engaged with the tube 3. A guiding member 13 may be provided outside of the distal end of the tube 3. As can be seen from the figure, the sleeve 12 is closer to the proximal end of the tube 3 relative to the guiding member 13.

More specifically, the distal end of the tube 3 may be configured as an expandable section 3*a* for accommodating an implantable instrument, and a connection section 3*b* is provided which is connected to the expandable section 3*a* and extends towards the proximal end. The sleeve 12, which is located around the connection section 3*b* of the tube 3, not only protects the tube 3, but also provides a new passage for the pull wire 8 extending towards the proximal end.

An important reason for providing the guiding sleeve which constrains the movable section 8*c* of the pull wire 8 is to avoid the movable section from cutting or scratching the aorta. Similarly, the other section, except for the movable section, of the pull wire should not cause damage to the aorta.

Figure 48:
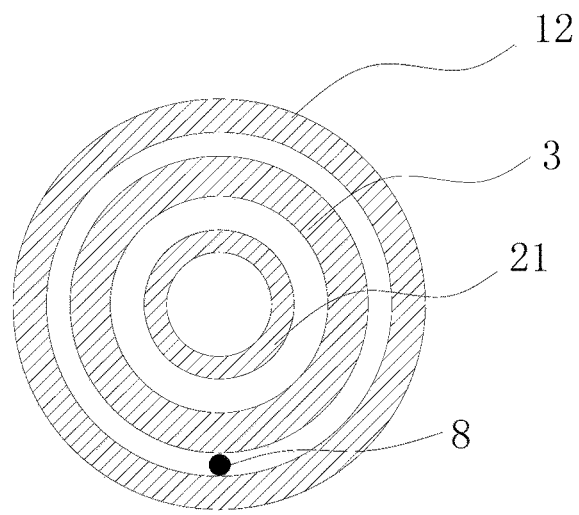
FIG. 48 is a cross-sectional view taken along A-A of FIG. 47.

Referring to FIG. 48, in one embodiment, the section of the pull wire 8 which is movable outside the tube is configured as a movable section, and the section which is connected to the proximal end of the movable section is configured as an extension section. The extension section extends towards the proximal end within the gap between the tube 3 and the sleeve 12, such that the extension section can be prevented from passing through the tube to affect the configuration of the tube. In order to achieve the desired effect, it is emphasized herein that all of the extension section is located within the gap between the tube 3 and the sleeve 12.

Figure 49:
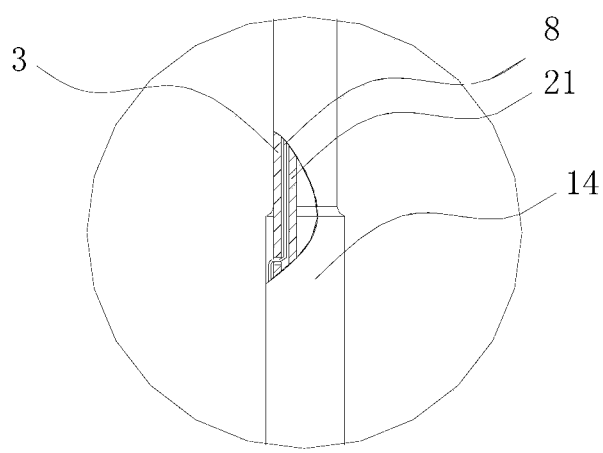
FIG. 49 is an enlarged view of part I of FIG. 47.

Referring to FIG. 49, another embodiment differs from the previous embodiment in that the connection portion between the movable section and the extension section passes through the outer wall of the tube 3, and the extension section extends towards the proximal end within the tube 3. In order to achieve the desired effect, it is emphasized herein that the extension section extends towards the proximal end and is entirely within the tube 2.

It should be noted that the connection portion between the movable section and the extension section is not a fixed portion of the pull wire, but is a relative concept referring to other components. For example, the connection portion between the movable section and the extension section passes through the wall of the tube. More precisely, the portion of the pull wire that passes through the wall of the tube is the connection portion between the movable section and the extension section.

It is easy to understand that the guiding sleeve 14 and the sleeve 12 that are provided on the tube, may be configured such that the proximal end of the guiding sleeve 14 and the distal end of the sleeve 12 are adjacent to or connected with each other. In the case where the two are adjacent to each other, there will be no constraint between the two, and thus the two will be flexible, which facilitates the arrangement between the two.

In the case where the proximal end of the guiding sleeve 14 and the distal end of the sleeve 12 are connected to each other to form one single piece, although the flexibility of the two will be reduced, the overall appearance can be improved. The two may be connected to each other by welding or in a detachable manner, and the two may be connected continuously or discontinuously.

The technical features of the above-mentioned embodiments can be combined arbitrarily. In order to make the description concise, not all possible combinations of the technical features in the above-mentioned embodiments are described. However, as long as there is no contradiction in the combination of these technical features, all should be considered as falling within the scope of the present disclosure.

The above-mentioned embodiments are only several embodiments of the present disclosure, and are described specifically and in detail, but they should not be interpreted as a limitation to the scope of the disclosure. It should be noted that for those skilled in the art, without departing from the concept of the present disclosure, a plurality of modifications and developments can be made, and these all fall within the protection scope of the present disclosure. Therefore, the protection scope of the present disclosure should be subject to the appended claims.

What is claimed is:

1. A bendable delivery system for an implantable valve, comprising:

a bendable sheath, comprising a tube and a pull wire, wherein the tube has a distal end and a proximal end, and the distal end of the tube is configured to be bent by the pull wire, and wherein one end of the pull wire extends towards the proximal end of the tube, a connection portion of the other end of the pull wire and the tube is located at or adjacent to the distal end of the tube, and at least one section of the pull wire is configured as a movable section which is movable outside of the tube; the tube comprises a first section at the distal end for accommodating an implantable instrument, and a connection section connected to the first section and extending towards the proximal end;

a sheath core arranged in the bendable sheath, and an operating handle connected to proximal ends of the bendable sheath and the sheath core; wherein a proximal end of the pull wire is connected with the operating handle;

wherein the sheath core comprises a core tube, and the core tube has a loading section at a distal end for placing the implantable instrument; before release, the first section of the bendable sheath is configured to surround the loading section; and wherein a distal end of the movable section is configured to enter an inner cavity of the tube from an outer wall of the tube through a first through hole, and then pass out of the tube from the inner cavity through a second through hole, and thereafter being knotted with a portion of the movable section outside the tube.

2. The bendable delivery system for an implantable valve according to claim 1, wherein the bendable sheath is further provided with a guiding member which functions between the tube and the movable section to delimit a gap between the tube and the movable section when bending.

3. The bendable delivery system for an implantable valve according to claim 2, wherein a plurality of the guiding members is provided which are spaced-apart from each other in an axial direction of the tube to form a plurality of guiding portions for delimiting the gap between the tube and the movable section.

4. The bendable delivery system for an implantable valve according to claim 2, wherein the guiding member is configured as a radial expandable structure, and has an undeformed configuration in which the guiding member constrains the movable section against the outer wall of the tube, and a deformed configuration in which the guiding member is locally separated from the tube under an action of the movable section.

5. The bendable delivery system for an implantable valve according to claim 2, wherein the guiding member is configured as a guiding sleeve that is connected around an outer periphery of the tube and surrounds the movable section.

6. The bendable delivery system for an implantable valve according to claim 5, wherein the guiding sleeve is configured as a coiled structure, and has a deformed configuration in which the guiding sleeve is locally separated from the tube under an action of the movable section and the corresponding portions of the coiled structure are unfolded, and an undeformed configuration in which the coiled structure automatically returns to drive the movable section to closely contact with the outer wall of the tube.

7. The bendable delivery system for an implantable valve according to claim 6, wherein the coiled structure in the undeformed configuration is coiled by more than one circle, and a portion extending beyond 360 degrees overlaps with a portion within 360 degrees.

8. The bendable delivery system for an implantable valve according to claim 6, wherein a starting end and a terminal end of the coiled structure that is coiled in a circumferential direction are connected by a flexible film.

9. The bendable delivery system for an implantable valve according to claim 5, wherein a distal end and a proximal end of the guiding sleeve are fixed on the outer periphery of the tube, and a section of the guiding sleeve between the distal end and the proximal end is movably arranged around the outer periphery of the tube.

10. The bendable delivery system for an implantable valve according to claim 5, wherein a distal end of the guiding sleeve is:
fixed on the connection section adjacent to the first section; or
fixed at a junction of the connection section and the first section; or
fixed on the first section and adjacent to a proximal end of the first section.

11. The bendable delivery system for an implantable valve according to claim 5, wherein a side wall of the guiding sleeve is provided with a reinforced area that contacts and engages with the movable section.

12. The bendable delivery system for an implantable valve according to claim 11, wherein the reinforced area has a larger thickness relative to the other neighboring area.

13. The bendable delivery system for an implantable valve according to claim 11, wherein a reinforcement layer is provided in a side wall of the reinforced area.

14. The bendable delivery system for an implantable valve according to claim 1, wherein the distal end of the movable section is:
fixed on the connection section adjacent to the first section; or
fixed at a junction of the connection section and the first section; or
fixed on the first section.

15. The bendable delivery system for an implantable valve according to claim 14, wherein the distal end of the movable section is fixed on the first section, and is close to a proximal end of the first section, or is close to a distal end of the first section, or is between the proximal end and the distal end of the first section.

16. The bendable delivery system for an implantable valve according to claim 1, wherein the pull wire is connected at the distal end of the tube, or less than 5 cm away from the distal end.

17. The bendable delivery system for an implantable valve according to claim 1, wherein the core tube is fixed with a guiding head at the distal end, and a fixing head for the implantable instrument adjacent to the guiding head, wherein the loading section is between the guiding head and the fixing head for the implantable instrument.

* * * * *